(12) United States Patent
Jacobine et al.

(10) Patent No.: US 7,705,064 B2
(45) Date of Patent: Apr. 27, 2010

(54) PHOTOSENSITIVE COMPOUNDS, PHOTOPOLYMERIZABLE COMPOSITIONS INCLUDING THE SAME, AND METHODS OF MAKING AND USING THE SAME

(75) Inventors: Anthony F. Jacobine, Meriden, CT (US); John G. Woods, Farmington, CT (US); Joel D. Schall, New Haven, CT (US); Steven T. Nakos, Andover, CT (US); Andrew D. Messana, Newington, CT (US); David M. Glaser, New Britain, CT (US)

(73) Assignee: Henkel Corporation, Rocky Hill, CT (US)

( * ) Notice: Subject to any disclaimer, the term of this patent is extended or adjusted under 35 U.S.C. 154(b) by 213 days.

(21) Appl. No.: 11/781,317

(22) Filed: Jul. 23, 2007

(65) Prior Publication Data

US 2009/0030106 A1    Jan. 29, 2009

(51) Int. Cl.
C08F 2/50 (2006.01)
C08F 222/10 (2006.01)
C07C 69/587 (2006.01)
C08G 16/00 (2006.01)

(52) U.S. Cl. .................. 522/36; 522/170; 522/173; 522/174; 522/182; 522/187; 522/100; 522/104; 522/90; 568/9; 568/303; 568/397

(58) Field of Classification Search .................. 522/33, 522/34, 36, 173, 174, 175, 182, 183, 170, 522/90, 100, 104; 568/8, 9, 303, 397
See application file for complete search history.

(56) References Cited

U.S. PATENT DOCUMENTS

| | | | |
|---|---|---|---|
| 4,058,400 A | 11/1977 | Crivello | 96/86 |
| 4,058,401 A | 11/1977 | Crivello | 96/115 |
| 4,151,056 A * | 4/1979 | Park | 522/89 |
| 4,219,654 A | 8/1980 | Crivello | 546/342 |
| 4,505,793 A | 3/1985 | Tamoto et al. | 204/159.16 |
| 5,015,678 A | 5/1991 | Seltzer et al. | |
| 5,079,378 A | 1/1992 | Crivello | 556/64 |
| 5,395,862 A | 3/1995 | Neckers et al. | 522/25 |
| 5,451,343 A | 9/1995 | Neckers et al. | 252/582 |
| 5,545,676 A | 8/1996 | Palazzotto et al. | 522/15 |
| 5,550,265 A | 8/1996 | Castellanos et al. | 556/7 |
| 5,668,192 A | 9/1997 | Castellanos et al. | 552/31 |
| 5,672,731 A | 9/1997 | Chen et al. | |
| 5,945,489 A | 8/1999 | Moy et al. | 525/471 |
| 6,025,410 A | 2/2000 | Moy et al. | 522/182 |
| 6,147,184 A | 11/2000 | Castellanos et al. | 528/410 |
| 6,153,661 A | 11/2000 | Castellanos et al. | 522/31 |
| 6,673,851 B2 | 1/2004 | Moy et al. | 522/173 |
| 7,166,648 B2 * | 1/2007 | Lachowicz et al. | 522/36 |
| 7,169,825 B2 * | 1/2007 | Narayan-Sarathy et al. | 522/13 |
| 7,304,112 B2 * | 12/2007 | Lewandowski et al. | 525/330.3 |
| 7,307,106 B2 * | 12/2007 | Fansler et al. | 522/34 |
| 7,317,061 B2 * | 1/2008 | Narayan-Sarathy et al. | 526/317.1 |
| 7,396,429 B2 * | 7/2008 | Beckley et al. | 156/275.7 |
| 7,407,707 B2 * | 8/2008 | Gould et al. | 428/418 |
| 2003/0073757 A1 | 4/2003 | Moy et al. | 522/176 |
| 2004/0029991 A1 | 2/2004 | Warmkessel et al. | 522/150 |
| 2005/0080162 A1 | 4/2005 | Narayan-Sarathy | 523/160 |
| 2005/0272830 A1 | 12/2005 | Gould et al. | |

FOREIGN PATENT DOCUMENTS

| | | |
|---|---|---|
| EP | 0 369 645 A1 | 5/1990 |
| EP | 0 563 925 A1 | 10/1993 |
| EP | 1 342 737 | 6/2007 |
| WO | PCT/FR97/00566 | 10/1997 |
| WO | PCT/FR98/00741 | 10/1998 |
| WO | WO 2004/011848 | 2/2004 |
| WO | PCT/US05/016900 | 1/2006 |

OTHER PUBLICATIONS

International Search Report for International PCT Application No. PCT/US2008/008886 mailed Feb. 17, 2009.
C. Macosko and D. Miller, Macromolecules 1976, 9(2), 199.

* cited by examiner

*Primary Examiner*—Susan W Berman
(74) *Attorney, Agent, or Firm*—Steven C. Bauman

(57) ABSTRACT

The present invention is directed to reaction products prepared from at least one Michael addition donor material including two or more active methylene hydrogens; and at least one material capable of reacting with a Michael addition donor, the material having one Michael addition acceptor and at least one functional group selected from the group consisting of hydroxy, hydroxyalkyl, vinyl ether, amino, aminoalkyl, carboxy, carboxyalkyl, cyano, and cyanoalkyl groups; or reaction products prepared from (a) at least one Michael addition donor material comprising at least one Michael Addition donor group selected from the group consisting of cyano functional groups and phosphono functional groups; and (b) at least one material capable of reacting with the at least one Michael addition donor group, the material having at least one Michael addition acceptor, wherein the above reaction products are capable of forming free radicals upon exposure to actinic radiation; as well as compositions, and processes for making and using the same.

35 Claims, 3 Drawing Sheets

PHOTOSENSITIVE COMPOUNDS, PHOTOPOLYMERIZABLE COMPOSITIONS INCLUDING THE SAME, AND METHODS OF MAKING AND USING THE SAME

BACKGROUND OF THE INVENTION

1. Field of the Invention

The present invention is directed to reaction products of Michael addition donor(s) and monoacrylate(s), the reaction product including at least one photolabile group, photopolymerizable compositions including the same, and methods related thereto.

2. Brief Description of Related Technology

Radiation curable adhesives and coatings containing (meth)acrylate monomers and oligomers and other free-radically polymerizable materials are widely used in applications where the cured material may come into contact directly or indirectly with food, drugs or medical devices. In such applications, it is desirable to ensure, to the extent that toxic or otherwise hazardous compounds are used in such products, that migration, evaporation or extraction of such materials from the cured material is controlled or ameliorated. A particular source of contamination in UV/visible light-cured products has been identified as residual unreacted photoinitiators and their decomposition products, such as benzaldehydes. Consequently, most commercially available photoinitiators are prohibited from use in such applications, examples of which include foil-laminating adhesives for food packaging, coil coatings for kitchen appliances and certain drug delivery/packaging systems.

For certain applications, users have employed electron beams (EB) instead of photoinitiator additives to cure such formulations. EB radiation is readily adsorbed by (meth) acrylate monomers and has sufficient photonic energy to initiate curing directly without the need for added photoinitiators. However, EB equipment is extremely expensive and can be used and justified only in certain applications in which production cost is not a primary consideration. Consequently, there is a need to develop UV and visible light curing additives and systems that produce cured materials having low extractables.

U.S. Pat. Nos. 5,945,489 and 6,025,410, U.S. Patent Application Publication No. 2005/0080162 and European Patent Application No. EP 1 342 737 disclose the reaction of an acetoacetate compound with an excess of a multi-functional acrylate to give an acrylated terminated oligomer containing a β-diketonic group incorporated into the polymer backbone. U.S. Pat. No. 6,673,851 and U.S. Patent Application Publication No. 2003/0073757 disclose subsequent reaction of such oligomers with a primary and/or secondary amines.

These oligomers undergo rapid UV initiated polymerization without the need for added photoinitiator, have good properties and are claimed to be suitable for flexible packaging adhesives, flexographic inks and screen-printing applications.

The process is, however, difficult to control at a manufacturing level and generally can result in non-uniform compositions with a variable content of gel particles. The reaction involves the stepwise addition of a multi-functional Michael donor (e.g. acetoacetate derivative) with a stoichiometric excess of a multifunctional Michael acceptor (e.g. diacrylate or polyacrylate) in the presence of a basic catalyst (e.g. tetramethylguanidine). The procedure can require care to avoid gelation, which can occur if the ratio of the equivalents of donor and acceptor groups, r, exceeds a value such that the fractional conversion required for gelation, alpha (α), is equal to or less than one, according to Equation 1:

$$r = 1/\alpha^2 (f_a - 1)(f_b - 1)$$  Equation 1 where $f_a$ and $f_b$ are the functionalities of the donor and acceptor groups. See C. Macosko and D. Miller, Macromolecules 1976, 9(2), 199. When the ratio r (also referred to as the stoichiometric imbalance; [donor]<[acceptor]) is chosen such that at full conversion of the Michael donor groups, the value of α>1, then gelation will not occur. For example, the ratio of acrylate to acetoacetate groups is generally required to be >2.5/1 for mono acetoacetates (difunctional) and triacrylates. Since the reaction is exothermic, it is usually required to slowly add the stoichiometrically deficient amount of donor species to a solution of the acceptor and catalyst at a rate that prevents a runaway thermal reaction. It is also required to ensure that very efficient mixing takes place during the addition to prevent the build-up of local high concentrations of the donor species, which would result in the formation of gel particles. At the initial stages of the reaction few difficulties are encountered, but as the oligomerization reaction proceeds, the viscosity increases significantly and efficient mixing becomes very difficult to achieve.

U.S. Patent Application Publication No. 2004/0029991 discloses UV curable acrylate terminated oligomers such as polyester acrylates, acrylate capped epoxy oligomers, polyacrylic acrylates, acrylate capped polyether polyols, acrylate terminated urethane oligomers or mixtures thereof. The acrylate terminated oligomers are prepared by first reacting a polyisocyanate with an acrylate having an isocyanate reactive group and then reacting the acrylate-isocyanate reaction product with an excess of polyol. The reaction conditions are held until no isocyanate functionality is detectable by titration in the reaction mixture. The acrylate capped urethane oligomer is then reacted with a Michael addition donor to form the UV curable oligomeric adhesive composition. The reaction is carried out in the presence of a base capable of promoting the Michael Addition reaction. On completion of the reaction, an acid can be added to the product to minimize viscosity buildup over time thus improving shelf life. In the production of such urethane resins, hydrogen bonding can undesirably increase the viscosity of the resin and mixing difficulties and residual basic catalyst can promote undesirable urethane reactions that limit the shelf-life of the resin.

There has been an ongoing desire to find photoinitiated adhesive compositions having good impact strength and toughness, because photocure mechanisms are ordinarily more rapid than heat cure mechanisms and can avoid heat degradation of the overall device, part and/or substrate.

SUMMARY OF THE INVENTION

In some embodiments, the present invention provides reaction products prepared from reactants comprising: (a) at least one Michael addition donor material comprising two or more active methylene hydrogens; and (b) at least one material capable of reacting with a Michael addition donor, the material having one Michael addition acceptor and comprising at least one functional group selected from the group consisting of hydroxy, hydroxyalkyl, vinyl ether, amino, aminoalkyl, carboxy, carboxyalkyl, cyano, and cyanoalkyl groups, wherein the reaction product is capable of forming free radicals upon exposure to actinic radiation.

In other embodiments, the present invention provides reaction products prepared from reactants comprising: (a) at least one Michael addition donor material comprising at least one Michael Addition donor group selected from the group consisting of cyano functional groups and phosphono functional groups; and (b) at least one material capable of reacting with the at least one Michael addition donor group, the material comprising at least one Michael addition acceptor, wherein the reaction product is capable of forming free radicals upon exposure to actinic radiation.

Also, the present invention provides compositions comprising the above reaction products, crosslinked polymer compositions prepared from the compositions, methods of preparing such compositions, and methods of using such compositions.

BRIEF DESCRIPTION OF THE FIGURES

The foregoing summary, as well as the following detailed description, will be better understood when read in conjunction with the appended drawings. In the drawings.

DETAILED DESCRIPTION OF THE INVENTION

Figure 1:
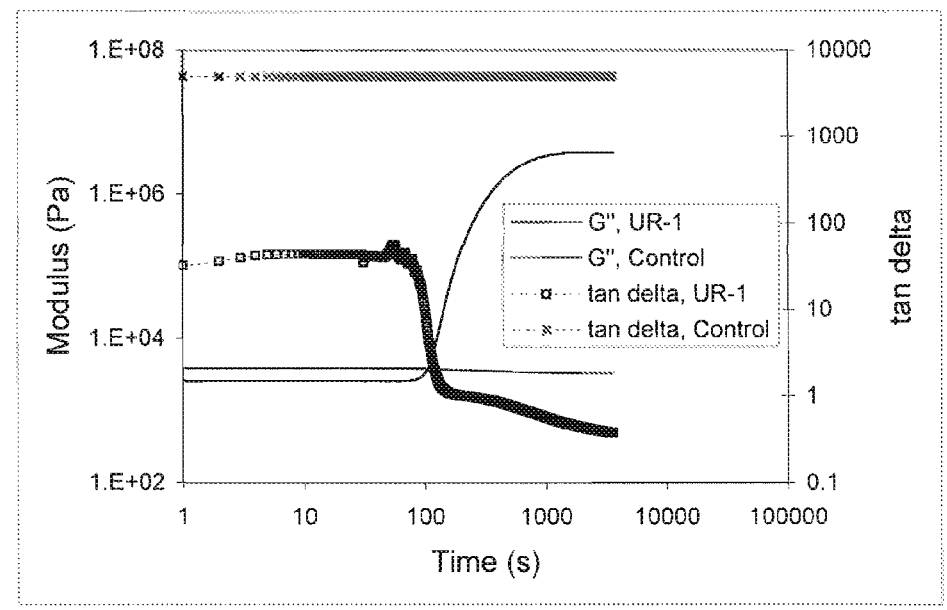
FIG. 1 is a graph of storage modulus (G') and tan δ (G"/G') as a function of UV exposure time for resin UR-1 according to the present invention and a control resin.

Other than in the operating examples, or where otherwise indicated, all numbers expressing quantities of ingredients, thermal conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values many be used.

Also, it should be understood that any numerical range recited herein is intended to include all sub-ranges subsumed therein. For example, a range of "1 to 10" is intended to include all sub-ranges between and including the recited minimum value of 1 and the recited maximum value of 10, that is, having a minimum value equal to or greater than 1 and a maximum value of equal to or less than 10.

As used herein, the term "composition" is intended to encompass a product comprising the specified ingredients in the specified amounts, as well as any product which results, directly or indirectly, from combination of the specified ingredients in the specified amounts.

As used herein, "formed from" or "prepared from" denotes open, e.g., "comprising," claim language. As such, it is intended that a composition "formed from" or "prepared from" a list of recited components be a composition comprising at least these recited components or the reaction product of at least these recited components, and can further comprise other, non-recited components, during the composition's formation or preparation.

As used herein, the phrase "reaction product of" means chemical reaction product(s) of the recited components, and can include partial reaction products as well as fully reacted products.

As used herein, the term "polymer" in meant to encompass oligomers, and includes without limitation both homopolymers and copolymers. The term "prepolymer" means a compound, monomer or oligomer used to prepare a polymer, and includes without limitation both homopolymer and copolymer oligomers. The term "oligomer" means a polymer consisting of only a few monomer units up to about ten monomer units, for example a dimer, trimer or tetramer.

As used herein, the term "cure" as used in connection with a composition, e.g., ("composition when cured" or a "cured composition", means that any curable or crosslinkable components of the composition are at least partially cured or crosslinked. In some non-limiting embodiments of the present invention, the chemical conversion of the crosslinkable components, i.e., the degree of crosslinking, ranges from about 5% to about 100% of complete crosslinking where complete crosslinking means full reaction of all crosslinkable components. In other non-limiting embodiments, the degree of crosslinking ranges from about 15% to about 80% or about 50% to about 60% of full crosslinking. One skilled in the art will understand that the presence and degree of crosslinking, i.e., the crosslink density, can be determined by a variety of methods, such as dynamic mechanical thermal analysis (DMA) using a IA Instruments DMA 2980 DMA analyzer over a temperature range of −65° F. (−18° C.) to 350° F. (177° C.) conducted under nitrogen according to ASTM D 4065-01. This method determines the glass transition temperature and crosslink density of free films of coatings or polymers. These physical properties of a cured material are related to the structure of the crosslinked network.

Curing of a polymerizable composition can be obtained by subjecting the composition to curing conditions, such as but not limited to irradiation, etc., leading to the reaction of reactive groups of the composition and resulting in polymerization and formation of a solid polymerizate. When a polymerizable composition is subjected to curing conditions, following polymerization and after reaction of most of the reactive groups occurs, the rate of reaction of the remaining unreacted reactive groups becomes progressively slower. In some non-limiting embodiments, the polymerizable composition can be subjected to curing conditions until it is at least partially cured. The term "at least partially cured" means subjecting the polymerizable composition to curing conditions, wherein reaction of at least a portion of the reactive groups of the composition occurs, to form a solid polymerizate. In some non-limiting embodiments, the polymerizable composition can be subjected to curing conditions such that a substantially complete cure is attained and wherein further exposure to curing conditions results in no significant further improvement in polymer properties, such as strength or hardness.

As used herein, "Michael addition" or "Michael reaction" is the nucleophilic addition of a carbanion to an alpha, beta unsaturated carbonyl compound, and is used to form C—C (carbon-carbon) bonds. A basic catalyst, such as triethylamine, can be used to catalyze the reaction. As used herein, "Michael Adduct" is the product(s) of the Michael addition reaction.

As used herein, "Michael addition donor material" means a compound, monomer or polymer containing one or more electron withdrawing groups which generate a carbanion which, acting as a nucleophile, attacks the conjugated bond of the alpha, beta unsaturated carbonyl compound. Non-limiting examples of such suitable electron withdrawing groups include carbonyl groups, cyano groups, phosphono groups, sulfinyl groups and sulfonyl groups. In some non-limiting embodiments, the Michael addition donor material can have one or more of these electron withdrawing groups or combinations of these groups, for example one acyl group and one phosphono group, or one acyl group and one sulfinyl group. As used herein, an "active methylene" means that the Michael addition donor material comprises two or more active methylene hydrogens, which form the carbanion on reaction with a base. A non-limiting example of a suitable group having active methylene hydrogens is an acetyl acetone group.

As used herein, "at least one material capable of reacting with a Michael addition donor, the material having one Michael addition acceptor" means a compound, monomer or polymer that has one Michael addition acceptor or alpha, beta unsaturated carbonyl group, such as an acrylate group, and can have other functionality as described herein.

While not intending to be bound by any theory, it is believed that the formation of self-initiating oligomers according to conventional prior art methods involves addition of multi-functional Michael donors to multi-functional Michael acceptors by a step-growth type mechanism. When the donor and acceptor are both difunctional, a linear, non-crosslinked oligomer or polymer is produced. If acrylate is used in excess, then an acrylate-terminated oligomer is obtained, as shown below:

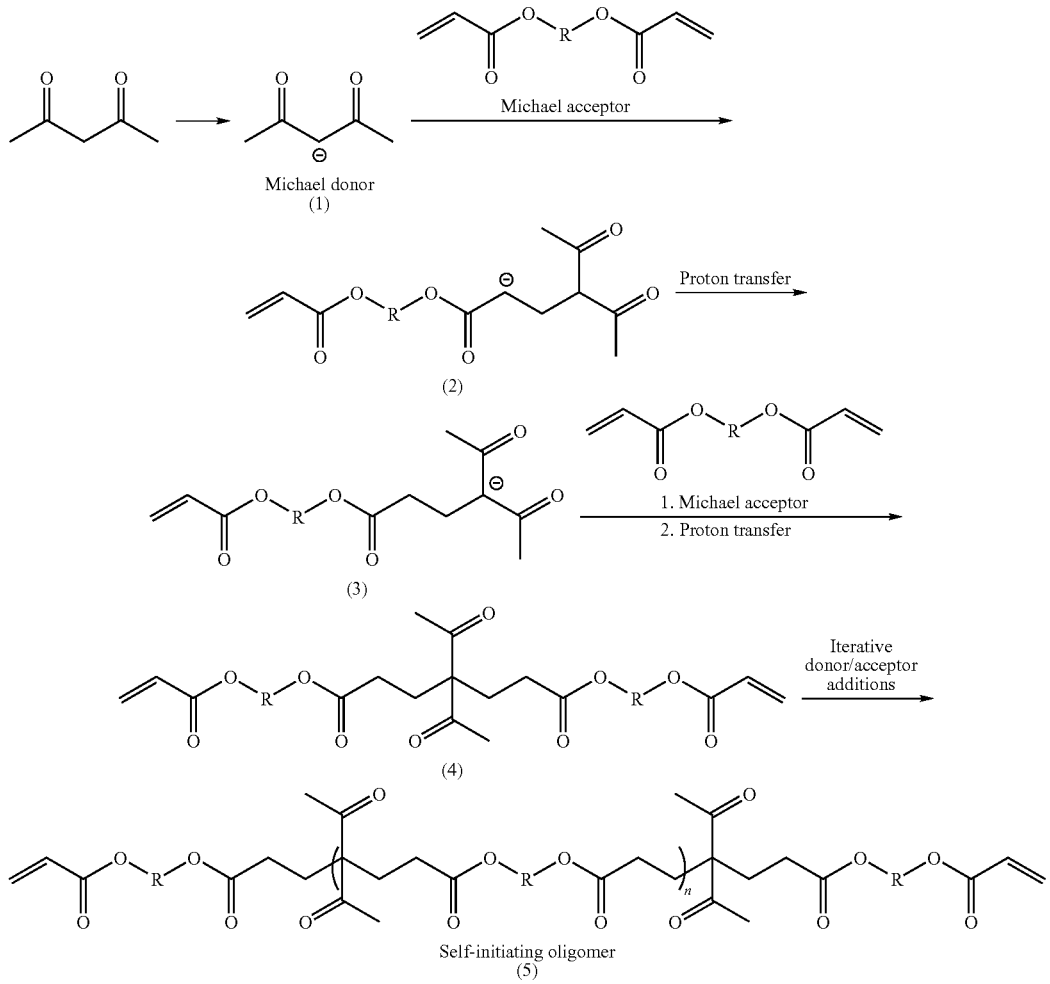

The reaction is initiated by formation of a stabilized donor anion of acetylacetone by reaction with basic catalyst (Reaction 1). Subsequent addition of the anion to one of the available acrylate groups occurs resulting in formation of unstabilized anion (Reaction 2), which undergoes proton transfer to more stabilized form (Reaction 3). The anion of Reaction 3 then adds to a second diacrylate, which after intramolecular proton transfer gives the β-diketo functionalized diacrylate indicated by Reaction 4. Iterative additions of donor and acceptor then produce the oligomeric species indicated by Reaction 5. The structure of this product consists of repeat units of alternating diaceto methylene and dipropionate esters.

When the average functionality of donor and acceptor species exceeds two, gelation may occur if the stoichiometric donor/acceptor ratio and reaction conversion exceed the threshold values for network formation. This process is shown below for a trifunctional acrylate and difunctional Michael donor:

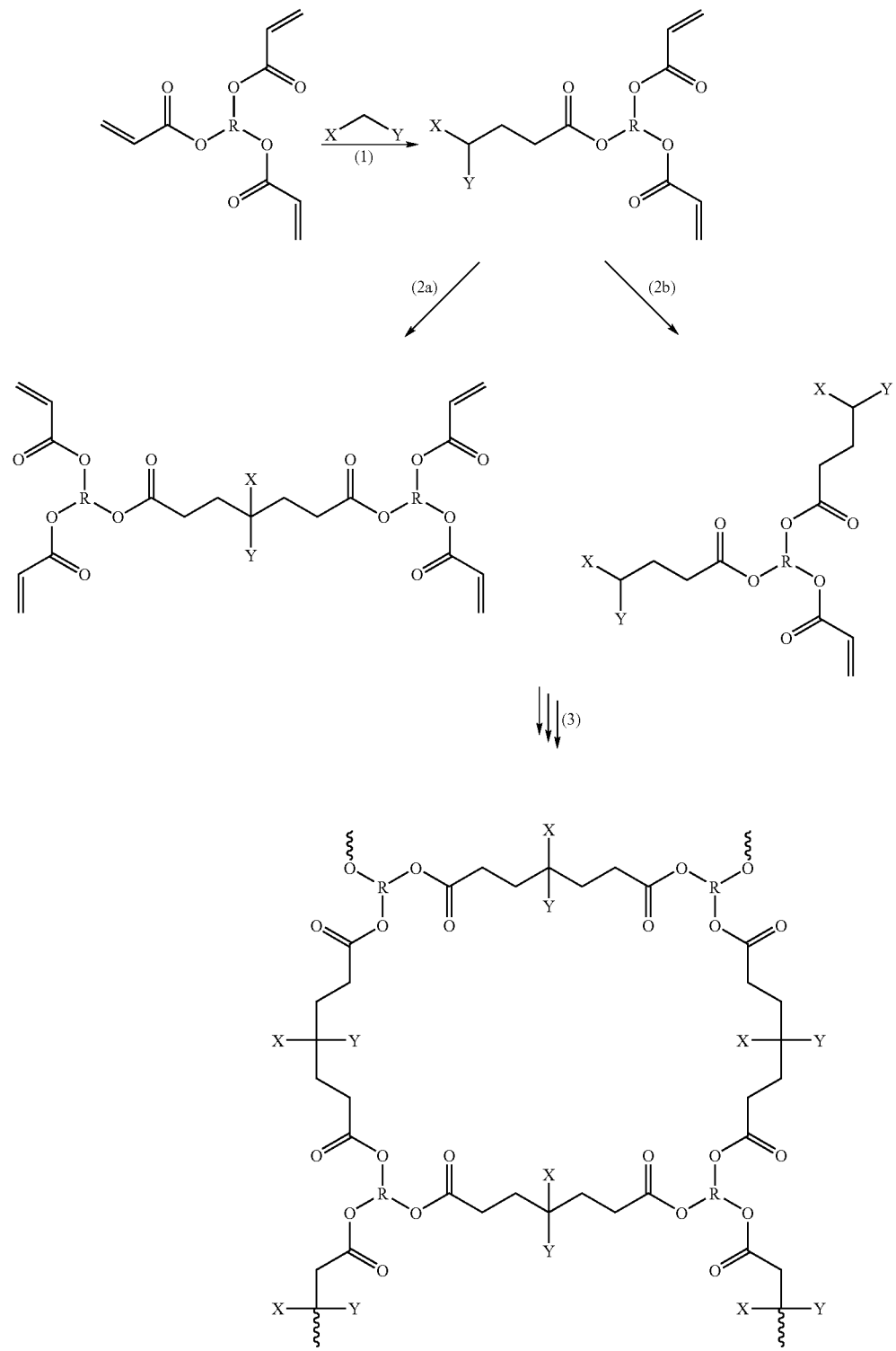

In this example, groups X and Y of active methylene compound denote electron withdrawing groups (acetyl, benzoyl, cyano, phosphono etc.), which may be the same (as in acetylacetone) or different (as in ethyl cyanoacetate). Reaction 1 depicts the initial adduct of one active methylene unit to one triacrylate. Reaction 2a depicts addition of a second triacrylate to initial adduct and 2b the addition of a second active methylene unit to the initial adduct. Subsequent additions result in progressive increases in molecular weight, branched oligomerization and eventual gelation (Reaction 3). In this example, the average functionality is 2.5 [(3+2)/2]. For a stoichiometric blend, gelation occurs when conversion exceeds 71% or at full conversion when the stoichiometric imbalance exceeds 0.5. The structure consists of repeat units of alternating methylene and tripropionate esters linked together in a 3-dimensional network.

In the conventional process discussed above, rapid mixing of the acceptor with the donor is used to minimize oligomerization and gellation. This, in theory, can prevent undesirable gellation. However, this process is inherently limited because of the engineering limitations of mixing.

The present inventors have discovered that using a monofunctional Michael addition acceptor material that contains groups reactive to other processes such as polyesterification, or urethane forming reactions, rather than a di- or polyacrylate, will not readily undergo the oligomerization process and gellation process that is observed when a di- or polyacrylate is used to make a self-initiating resin.

These self-initiating extender materials allow for the preparation of a broader range of oligomers and polymers and are not limited to acrylate oligomers. These extenders also allow for much greater control over the incorporation of the self-initiating group into the oligomer or polymer. This is important since polymer properties and derived adhesive and coating properties are dependent on the oligomer structure. Use of these materials allows much more control over polymer architecture, polymer properties, and derived adhesive properties.

As noted above, in some embodiments the present invention provides reaction products prepared from reactants comprising: (a) at least one Michael addition donor material comprising two or more active methylene hydrogens; and (b) at least one material capable of reacting with a Michael addition donor, the material having one Michael addition acceptor and comprising at least one functional group selected from the group consisting of hydroxy, hydroxyalkyl, vinyl ether, amino, aminoalkyl, carboxy, carboxyalkyl, cyano, and cyanoalkyl groups, wherein the reaction product is capable of forming free radicals upon exposure to actinic radiation, such as photolabile groups.

Self-initiating resins of the present invention containing photosensitive groups can be prepared by an alternative route that avoids the problems of gelation and shelf stability described above. The advantage of this method is that gelation is not possible during the Michael addition step, since material having one Michael addition acceptor is used. In addition, the Michael adducts are relatively low in molecular weight and viscosity, which greatly simplifies the neutralization or removal of the catalysts prior to reaction with polyisocyanate for production of urethane. This provides acrylated urethane resins with good shelf-stability, self-initiating properties and higher donor/acceptor ratios than is possible with existing systems.

This process is illustrated by the following non-limiting, simplified reaction scheme, in which a Michael addition donor material having two active methylene hydrogens is reacted with a monofunctional Michael acceptor material (a hydroxy functional acrylate) to form a Michael adduct that can be used as a self-initiating extender in subsequent polymerization:

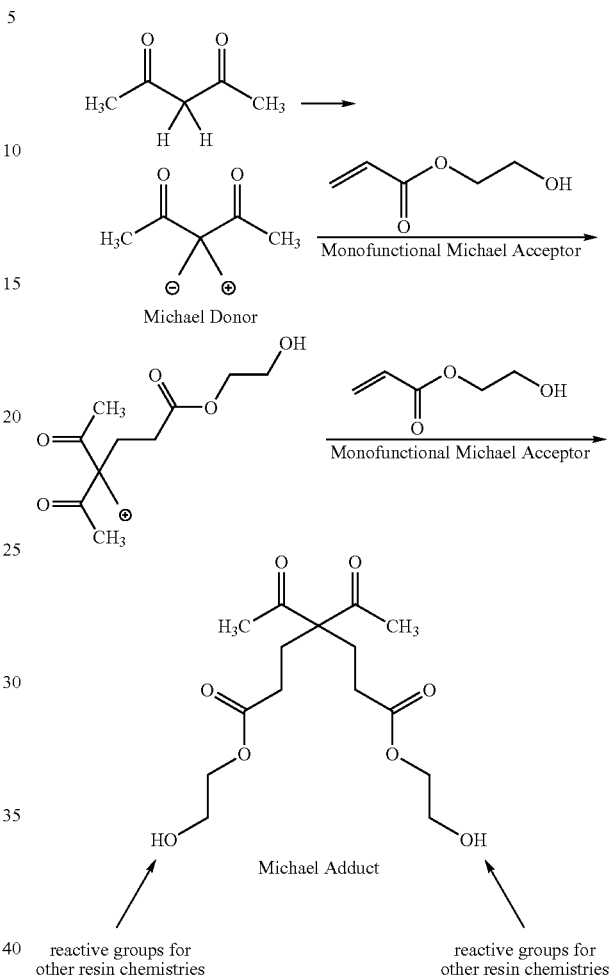

One skilled in the art would understand that other monofunctional Michael Acceptor materials can be used instead of 2-hydroxyethyl acrylate to provide functionalities other than hydroxyalkyl on the Michael Adduct, as discussed in detail below.

In some non-limiting embodiments, a Michael addition reaction of a hydroxy-functional monoacrylate and active methylene compound is carried out to give an intermediate polyol that is subsequently converted into a urethane acrylate resin with photoinitiating groups attached to the backbone of the oligomer structure.

As discussed above, in some non-limiting embodiments the reactants comprise at least one Michael addition donor material comprising two or more active methylene hydrogens and has at least two electron-withdrawing groups. In some non-limiting embodiments, the electron withdrawing group can be independently selected from carbonyl groups, cyano groups, phosphono groups, sulfinyl groups and/or sulfonyl groups. Combinations of any of the above groups can be used.

In some embodiments, non-limiting examples of suitable carbonyl groups are selected from acyl groups, keto groups, amide groups, ester groups and thiocarbonyl groups.

In some embodiments, non-limiting examples of suitable acyl groups are selected from the group consisting of alkyl ketones, heteroalkyl ketones, cycloalkyl ketones, heterocyclyl ketones, aryl ketones and heteroaryl ketones.

As used herein, "alkyl" means an aliphatic hydrocarbon group which may be straight or branched and comprising about 1 to about 20 carbon atoms in the chain, or about 1 to about 6 carbon atoms in the chain. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. "Heteroalkyl" means that the alkyl group is interrupted or substituted with one or more heteroatoms, such as halo, N, S or O. Non-limiting examples of suitable alkyl groups include methyl, ethyl, n-propyl, isopropyl and t-butyl.

"Cycloaliphatic" or "cycloalkyl" means a non-aromatic mono- or multicyclic ring system comprising about 3 to about 10 carbon atoms, or about 5 to about 10 carbon atoms. The cycloalkyl can be optionally substituted with one or more "ring system substituents" which may be the same or different, and are as defined herein. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Heterocyclic" or "heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. The prefix aza, oxa or thia before the heterocyclyl root name means that at least a nitrogen, oxygen or sulfur atone respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like.

"Aryl" means an aromatic monocyclic or multicyclic ring system comprising about 6 to about 14 carbon atoms, preferably about 6 to about 11 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multiclic ring system comprising about 5 to about 14 ring atoms, preferably about 5 to about 10 ring atoms, in which one or more of the ring atoms is an element other than carbon, for example nitrogen, oxygen or sulfur, alone or in combination. In some embodiments, the heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least one of a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazoolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moieties are methylene dioxy, ethylenedioxy, —C(CH$_3$)$_2$— and the like which form moieties such as, for example:

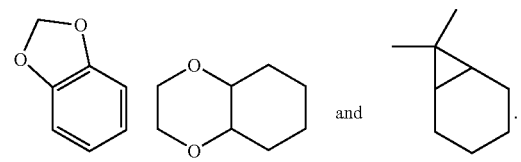

In some embodiments, non-limiting examples of compounds including suitable alkyl ketones include 2,4-pentanedione and 2,4,6-heptanetrione. In some embodiments, non-limiting examples of compounds including suitable heteroalkyl ketones include acetoacetamide, methyl acetoacetate, ethyl acetoacetate, butyl acetoacetate, butanediol diacetoacetate, ethylhexyl acetoacetate, lauryl acetoacetate, hexanediol diacetoacetate, neopentyl glycol diacetoacetate, trimethylolpropane triacetoacetate, glycerin triacetoacetate, pentaerythritol tetraacetoacetate, ethylene glycol monoacetoacetate mono(meth)acrylate and 1-(triethylphosphonomethyl)methyl ketone. In some embodiments, non-limiting examples of compounds including suitable cycloalkyl ketones include 4,4-dimethylcyclohexane-1,3-dione and 5,5-dimethylcyclohexane-1,3-dione. In some embodiments, non-limiting examples of compounds including suitable aryl ketones include dibenzoylmethane, benzoylacetone, benzoylacetamide and benzoylacetanilide.

In some non-limiting embodiments, the Michael addition donor material comprises at least one ester group. Non-limiting examples of compounds including suitable ester groups include dimethyl acetonedicarboxylate, diethyl acetonedicarboxylate, 2,2-dimethyl-1,3-dioxane-4,6-dione and malonic diesters.

In some non-limiting embodiments, the Michael addition donor material comprises at least one keto group. Non-limiting examples of compounds including suitable keto groups include acetoacetates such as are listed above, methyl acryloylmethyl ketone, ethyl acryloylmethyl ketone, isopropyl acryloylethyl ketone and acetoacetoxyethyl acrylate.

In some non-limiting embodiments, the Michael addition donor material comprises at least one amide group. Non-limiting examples of compounds including suitable amide groups include acetoacetamide, N-methylacetamide, N,N-diethylacetamide and benzoylacetamide.

In some non-limiting embodiments, the Michael addition donor material comprises at least one cyano group. Non-limiting examples of compounds including suitable cyano groups include malononitrile, ethyl cyanoacetate, methyl cyanoacetate and isobutyl cyanoacetate.

In some non-limiting embodiments, the Michael addition donor material comprises at least one phosphono group. Non-limiting examples of compounds including suitable phosphono groups include 1-(diethyl phosphonomethyl)-2-propanone, diethylphosphonomethyl methyl ketone, (diphenyl phosphonomethyl)-2-propanone, tetraethyl methylenebisphosphonate, triethyl phosphonoacetate and diethyl cyanomethylphosphonate.

In some non-limiting embodiments, the Michael addition donor material comprises at least one sulfonyl group. Non-limiting examples of compounds including suitable sulfonyl groups include phenylsulfonyl acetonitrile and diphenylsulfonyl methane.

As discussed above, the Michael addition donor material is reacted with at least one material capable of reacting with a Michael addition donor, referred to herein as the "Michael addition acceptor material". The Michael addition acceptor material has one Michael addition acceptor, or alpha, beta unsaturated carbonyl group, such as an acrylate group, methacrylate group, maleimide group, cinnamate group, crotonate group, acrylamide group, vinyl phosphonate group or vinyl sulfonate group, and can have other functionality as described herein.

In some non-limiting embodiments, the Michael addition acceptor material is a monoacrylate. In some non-limiting embodiments, the Michael addition acceptor material or monoacrylate can comprise at least one functional group selected from the group consisting of hydroxy, hydroxyalkyl vinyl ether, amino, aminoalkyl, carboxy, carboxyalkyl, cyano, and cyanoalkyl groups. Combinations of different functional groups can be used.

Non-limiting examples of suitable hydroxyalkyl functional monoacrylates include hydroxymethyl(meth)acrylate, hydroxyethyl(meth)acrylate, hydroxypropyl(meth)acrylate, hydroxybutyl(meth)acrylate, hydroxypentyl(meth)acrylate and hydroxypropoxypropyl(meth)acrylate.

A non-limiting example of a suitable vinyl ether functional monoacrylate is 2-(2'-Vinyloxy ethoxy)ethyl acrylate.

Non-limiting examples of suitable amino functional monoacrylates include protected amino functional monoacrylates such as 2-methylcarbamatoalkyl acrylate, ethylcarbamatoalkyl acrylate, propylcarbamatoalkyl acrylate, butylcarbamatoalkyl acrylate and isocyanatoethyl(meth) acrylate.

Non-limiting examples of suitable carboxy functional monoacrylates include acrylic acid, beta-carboxyethyl acrylate, and the reaction product of a hydroxy functional monoacrylate with a cyclic anhydride, such as succinic anhydride and tetrahydrophthalic anhydride.

In some non-limiting embodiments, the Michael addition acceptor material is an acrylamide, such as a hydroxy functional acrylamide. Non-limiting examples of suitable hydroxy functional acrylamides include N-methylol acrylamide and N-(2-hydroxyethyl)acrylamide.

In some non-limiting embodiments, the equivalent ratio of the Michael addition acceptor material to the Michael addition donor material can be at least about 1:1 to about 4:1, or about 2:1.

In some non-limiting embodiments, the reaction product, or Michael Adduct, is the reaction product is prepared from 2,4-pentanedione and 2-hydroxyethyl acrylate.

In some non-limiting embodiments, the reaction product, or Michael Adduct, is prepared from 2,4-pentanedione and 2-hydroxypropyl acrylate.

In some non-limiting embodiments, the reaction product, or Michael Adduct, is prepared from 4,4-dimethyl-1,3-cyclohexanedione and 2-hydroxybutyl acrylate.

In some non-limiting embodiments the reactants can further comprise minor amounts of at least one multifunctional (di- or higher-functional) Michael addition acceptor such that the relative amount of acceptor added, as defined by the stoichiometric imbalance, is selected such that $\alpha \geqq 1$ at full conversion of donor and gelation does not occur. In some embodiments, the multifunctional Michael addition acceptor can be a diacrylate or polyacrylate, for example diethylene glycol diacrylate, 1,6-hexanediol diacrylate, neopentyl glycol diacrylate, polyethylene glycol diacrylate, trimethylolpropane diacrylate.

In other embodiments, the reaction product can be prepared from reactants comprising: (a) at least one Michael addition donor material comprising at least one Michael Addition donor group selected from the group consisting of cyano functional groups and phosphono functional groups; and (b) at least one material capable of reacting with the at least one Michael addition donor group, the material comprising at least one Michael addition acceptor, wherein the reaction product is capable of forming free radicals upon exposure to actinic radiation. Suitable Michael addition donor materials comprising cyano functional groups and/or phosphono functional groups are discussed above, Other functional groups can be present, as discussed above. Suitable Michael addition acceptor materials include the monofunctional Michael Addition acceptor materials discussed above and/or multifunctional Michael Addition acceptor materials discussed above. The amounts of reactants used are similar to those discussed above.

As discussed above, the reactants can further comprise one or more basic catalysts, such as triethylamine, 1,1,3,3-tetramethylguanidine, 1,5-diazabicyclo[4.3.0]non-5-ene, 1,8-diazabicylco[5.4.0]undec-7-ene, benzyltrimethylammonium hydroxide, piperidine, potassium carbonate, sodium methoxide, or potassium tert-butoxide, to catalyze the reaction. The amount of basic catalyst can range from about 0.05 to about 5 weight percent of the total weight of the reactants.

In some non-limiting embodiments, the reaction product can be an oligomer or polymer having a number average molecular weight of about 500 to about 10,000 grams/mole.

The reaction product ("Michael Adduct") can be prepared from the reactants discussed above by any suitable Michael addition process well known to those skilled in the art. In a non-limiting example, the Michael Addition donor material can be mixed with a base, stirred and cooled to near 0° C. The Michael Addition acceptor material can be added slowly while maintaining the temperature near 0° C. After the addition is complete, the mixture can be warmed, for example to about 40° C., and stirred for until the reaction is essentially complete, for example from about 48 to about 72 hours. IR analysis can be used to confirm complete consumption of acrylate double bonds by the absence of absorption at 1630 cm$^{-1}$. The mixture can cooled to room temperature, dissolved in a solvent such as ethanol and treated with an agent, such as acidic alumina, to remove the catalyst. The mixture can be filtered to provide a clear solution and the solvent can be removed by distillation under reduced pressure (for example, 40° C.; ~200 torr) followed by heating in an oven under vacuum (for example, 80° C.; ~0.4 torr) to constant weight.

In some embodiments, the Michael Adduct can be useful as an initiator for generating free radicals to facilitate crosslinking of crosslinkable materials as discussed below.

In some non-limiting embodiments, a composition is provided that comprises (a) the Michael Adduct discussed above and (b) at least one material ("material (b)") capable of reacting with one or more of the functional groups (hydroxy, hydroxyalkyl, vinyl ether, amino, aminoalkyl, carboxy, carboxyalkyl, cyano, and/or cyanoalkyl groups) of the Michael Adduct. The Michael Adduct and material (b) can be reacted under suitable conditions well known to those skilled in the art and as discussed below to form Reaction Product A.

In some non-limiting embodiments, the Michael Adduct can comprise about 0.5 to about 10 weight percent, or about 0.5 to about 5 weight percent, of the composition on a basis of total weight of the components used to prepare the composition.

In some non-limiting embodiments, the material (b) can be selected from:

(i) at least one isocyanate functional material, wherein the Michael Adduct is hydroxyalkyl, primary aminoalkyl, or secondary aminoalkyl functional;

(ii) at least one epoxy functional material, wherein the Michael Adduct is carboxylic acid, primary aminoalkyl, or secondary aminoalkyl functional;

(iii) at least one carboxylic acid functional material, wherein the Michael Adduct is hydroxyalkyl functional;

(iv) at least one anhydride functional material, wherein the Michael Adduct is hydroxyalkyl, primary aminoalkyl, or secondary aminoalkyl functional; and (v) at least one acid halide functional material, wherein the Michael Adduct is hydroxyalkyl, primary aminoalkyl, or secondary aminoalkyl functional.

As used herein, the term "isocyanate functional material" includes compounds, monomers, oligomers and polymers comprising at least one or at least two —N=C=O functional groups and/or at least one or at least two —N=C=S (isothiocyanate) groups. Monofunctional isocyanates can be used as chain terminators or to provide terminal groups during polymerization. As used herein, "polyisocyanate" means an isocyanate comprising at least two —N=C=O functional groups, such as diisocyanates or triisocyanates, as well as dimers and trimers or biurets of the isocyanates, and mixtures thereof. Suitable isocyanates are capable of forming a covalent bond with a reactive group such as hydroxy functional group. Isocyanates useful in the present invention can be branched or unbranched.

Isocyanates useful in the present invention include "modified", "unmodified" and mixtures of "modified" and "unmodified" isocyanates. The isocyanates can have "free", "blocked" or partially blocked isocyanate groups. The term "modified" means that the aforementioned isocyanates are changed in a known manner to introduce biuret, urea, carbodiimide, urethane or isocyanurate groups or blocking groups. In some non-limiting embodiments, the "modified" isocyanate is obtained by cycloaddition processes to yield dimers and trimers of the isocyanate, i.e., polyisocyanates. Free isocyanate groups are extremely reactive. In order to control the reactivity of isocyanate group-containing components, the NCO groups may be blocked with certain selected organic compounds that render the isocyanate group inert to reactive hydrogen compounds at room temperature. When heated to elevated temperatures, e.g., ranging from about 90° C. to about 200° C., the blocked isocyanates release the blocking agent and react in the same way as the original unblocked or free isocyanate.

Generally, compounds used to block isocyanates are organic compounds that have active hydrogen atoms, e.g., volatile alcohols, epsilon-caprolactam or ketoxime compounds. Non-limiting examples of suitable blocking compounds include phenol, cresol, nonylphenol, epsilon-caprolactam and methyl ethyl ketoxime.

As used herein, the NCO in the NCO:OH ratio represents the free isocyanate of free isocyanate-containing materials, and of blocked or partially blocked isocyanate-containing materials after the release of the blocking agent. In some cases, it is not possible to remove all of the blocking agent. In those situations, more of the blocked isocyanate-containing material would be used to attain the desired level of free NCO.

The molecular weight of the isocyanate functional material can vary widely. In alternate non-limiting embodiments, the number average molecular weight (Mn) of each can be at least about 100 grams/mole, or at least about 150 grams/mole, or less than about 15,000 grams/mole, or less than about 5,000 grams/mole. The number average molecular weight can be determined using known methods, such as by gel permeation chromatography (GPC) using polystyrene standards.

Non-limiting examples of suitable isocyanate functional materials include aliphatic, cycloaliphatic, aromatic and heterocyclic isocyanates, dimers and trimers thereof, and mixtures thereof. When an aromatic polyisocyanate is used, generally care should be taken to select a material that does not cause the polyurethane to color (e.g., yellow).

In some non-limiting embodiments, the aliphatic and cycloaliphatic diisocyanates can comprise about 6 to about 100 carbon atoms linked in a straight chain or cyclized and having two isocyanate reactive end groups.

Non-limiting examples of suitable aliphatic isocyanates include straight chain isocyanates such as ethylene diisocyanate, trimethylene diisocyanate, 1,6-hexamethylene diisocyanate (HDI), tetramethylene diisocyanate, hexamethylene diisocyanate, octamethylene diisocyanate, nonamethylene diisocyanate, decamethylene diisocyanate, 1,6,11-undecanetriisocyanate, 1,3,6-hexamethylene triisocyanate, bis(isocyanatoethyl)-carbonate, and bis(isocyanatoethyl)ether.

Other non-limiting examples of suitable aliphatic isocyanates include branched isocyanates such as trimethylhexane diisocyanate, trimethylhexamethylene diisocyanate (TMDI), 2,2'-dimethylpentane diisocyanate, 2,2,4-trimethylhexane diisocyanate, 2,4,4,-trimethylhexamethylene diisocyanate, 1,8-diisocyanato-4-(isocyanatomethyl)octane, 2,5,7-trimethyl-1,8-diisocyanato-5-(isocyanatomethyl)octane, 2-isocyanatopropyl-2,6-diisocyanatohexanoate, lysinediisocyanate methyl ester and lysinetriisocyanate methyl ester.

Non-limiting examples of suitable cycloaliphatic isocyanates include dinuclear compounds bridged by an isopropylidene group or an alkylene group of 1 to 3 carbon atoms. Non-limiting examples of suitable cycloaliphatic isocyanates include 1,1'-methylene-bis-(4-isocyanatocyclohexane) or 4,4'-methylene-bis-(cyclohexyl isocyanate) (such as DESMODUR W commercially available from Bayer Corp.), 4,4'-isopropylidene-bis-(cyclohexyl isocyanate), 1,4-cyclohexyl diisocyanate (CHDI), 4,4'-dicyclohexylmethane diisocyanate, 3-isocyanato methyl-3,5,5-trimethylcyclohexyl isocyanate (a branched isocyanate also known as isophorone diisocyanate or IPDI) which is commercially available from Arco Chemical Co. and meta-tetramethylxylylene diisocyanate [a branched isocyanate also known as 1,3-bis(1-isocyanato-1-methylethyl)-benzene which is commercially available from Cytec Industries Inc. under the tradename TMXDI (Meta) Aliphatic Isocyanate] and mixtures thereof.

Other useful dinuclear cycloaliphatic diisocyanates include those formed through an alkylene group of from 1 to 3 carbon atoms inclusive, and which can be substituted with nitro, chlorine, alkyl, alkoxy and other groups that are not reactive with hydroxyl groups (or active hydrogens) providing they are not positioned so as to render the isocyanate group unreactive. Also, hydrogenated aromatic diisocyanates such as hydrogenated toluene diisocyanate may be used. Dinuclear diisocyanates in which one of the rings is saturated and the other unsaturated, which are prepared by partially hydrogenating aromatic diisocyanates such as diphenyl methane diisocyanates, diphenyl isopropylidene diisocyanate and diphenylene diisocyanate, may also be used.

Mixtures of cycloaliphatic diisocyanates with aliphatic diisocyanates and/or aromatic diisocyanates may also be used. An example is 4,4'-methylene-bis-(cyclohexyl isocyanate) with commercial isomer mixtures of toluene diisocyanate or meta-phenylene diisocyanate.

Thioisocyanates corresponding to the above diisocyanates can be used, as well as mixed compounds containing both an isocyanate and a thioisocyanate group.

Non-limiting examples of suitable isocyanate functional materials can include but are not limited to DESMODUR W, DESMODUR N 3300 (hexamethylene diisocyanate trimer), DESMODUR N 3400 (60% hexamethylene diisocyanate dimer and 40% hexamethylene diisocyanate trimer), which are commercially available from Bayer Corp.

Other non-limiting examples of suitable polyisocyanates include ethylenically unsaturated polyisocyanates; alicyclic polyisocyanates; aromatic polyisocyanates; aliphatic polyisocyanates; halogenated, alkylated, alkoxylated, nitrated, carbodiimide modified, urea modified and biuret modified derivatives of isocyanates; and dimerized and trimerized products of isocyanates.

Non-limiting examples of suitable ethylenically unsaturated polyisocyanates include butene diisocyanate and 1,3-butadiene-1,4-diisocyanate. Non-limiting examples of suitable alicyclic polyisocyanates include isophorone diisocyanate, cyclohexane diisocyanate, methylcyclohexane diisocyanate, bis(isocyanatomethyl)cyclohexane, bis(isocyanatocyclohexyl)methane, bis(isocyanatocyclohexyl)-2,2-propane, bis(isocyanatocyclohexyl)-1,2-ethane, 2-isocyanatomethyl-3-(3-isocyanatopropyl)-5-isocyanatomethyl-bicyclo[2.2.1]-heptane, 2-isocyanatomethyl-3-(3-isocyanatopropyl)-6-isocyanatomethyl-bicyclo[2.2.1]-heptane, 2-isocyanatomethyl-2-(3-isocyanatopropyl)-5-isocyanatomethyl-bicyclo[2.2.1]-heptane, 2-isocyanatomethyl-2-(3-isocyanatopropyl)-6-isocyanatomethyl-bicyclo[2.2.1]-heptane, 2-isocyanatomethyl-3-(3-isocyanatopropyl)-6-(2-isocyanatoethyl)-bicyclo[2.2.1]-heptane, 2-isocyanatomethyl-2-(3-isocyanatopropyl)-5-(2-isocyanatoethyl)-bicyclo[2.2.1]-heptane and 2-isocyanatomethyl-2-(3-isocyanatopropyl)-6-(2-isocyanatoethyl)-bicyclo[2.2.1]-heptane.

Non-limiting examples of suitable aromatic polyisocyanates include α,α'-xylene diisocyanate, bis(isocyanatoethyl)benzene, α,α,α',α'-tetramethylxylene diisocyanate, 1,3-bis(1-isocyanato-1-methylethyl)benzene, bis(isocyanatobutyl)benzene, bis(isocyanatomethyl)naphthalene, bis(isocyanatomethyl)diphenyl ether, bis(isocyanatoethyl) phthalate, mesitylene triisocyanate and 2,5-di(isocyanatomethyl)furan, phenylene diisocyanate, ethylphenylene diisocyanate, isopropylphenylene diisocyanate, dimethylphenylene diisocyanate, diethylphenylene diisocyanate, diisopropylphenylene diisocyanate, trimethylbenzene triisocyanate, benzene diisocyanate, benzene triisocyanate, naphthalene diisocyanate, methylnaphthalene diisocyanate, biphenyl diisocyanate, toluidine diisocyanate, tolylidine diisocyanate, tolylene diisocyanate, 4,4'-diphenylmethane diisocyanate, bis(3-methyl-4-isocyanatophenyl)methane, bis(isocyanatophenyl)ethylene, 3,3'-dimethoxy-biphenyl-4,4'-diisocyanate, triphenylmethane triisocyanate, polymeric 4,4'-diphenylmethane diisocyanate, naphthalene triisocyanate, diphenylmethane-2,4,4'-triisocyanate, 4-methyldiphenylmethane-3,5,2',4',6'-pentaisocyanate, diphenylether diisocyanate, bis(isocyanatophenylether)ethyleneglycol, bis(isocyanatophenylether)-1,3-propyleneglycol, benzophenone diisocyanate, carbazole diisocyanate, ethylcarbazole diisocyanate and dichlorocarbazole diisocyanate.

In some non-limiting embodiments, the isocyanate functional material comprises at least one triisocyanate or at least one polyisocyanate trimer. Non-limiting examples of such isocyanates include aromatic triisocyanates such as tris(4-iso-cyanatophenyl)methane (DESMODUR R). 1,3,5-tris(3-isocyanato-4-methylphenyl)-2,3,6-trioxohexahydro-1,3,5 triazine (DESMODUR IL); adducts of aromatic diisocyanates such as the adduct of 2,4-tolylene diisocyanate (TDI, 2,4-diisocyanatotoluene) and trimethylolpropane (DESMODUR L); and from aliphatic triisocyanates such as N-isocyanatohexylaminocarbonyl-N,N'-bis(isocyanatohexyl)urea (DESMODUR N), 2,4,6-trioxo-1,3,5-tris(6-isocyanatohexyl)hexahydro-1,3,5-triazine (DESMODUR N3390), 2,4,6-trioxo-1,3,5-tris(5-isocyanato-1,3,3-trimethylcyclo-hexyl-methyl)hexahydro-1,3,5-triazine (DESMODUR Z4370), and 4-(isocyanatomethyl)-1,8-octane diisocyanate. The above DESMODUR products are commercially available from Bayer Corp. Also useful are the biuret of hexanediisocyanate, polymeric methane diisocyanate, and polymeric isophorone diisocyanate. Trimers of hexamethylene diisocyanate, isophorone diisocyanate and tetramethylxylylene diisocyanate.

In some non-limiting embodiments, the isocyanate functional material is a cycloaliphatic compound, such as a dinuclear compound bridged by an isopropylidene group or an alkylene group of 1 to 3 carbon atoms.

In some embodiments, the isocyanate functional material is a diisocyanate, such as methylene bis(phenyl isocyanate) (also known as MDI), 2,4-toluene diisocyanate (2,4-TDI); a 80:20 mixture of 2,4- and 2,6-toluene diisocyanate (also known as TDI); 3-isocyanatomethyl-3,5,5-trimethyl cyclohexylisocyanate (IPDI); m-tetramethyl xylene diisocyanate (TMXDI); hexamethylene diisocyanate (HDI); and 4,4'-methylene-bis-(cyclohexyl isocyanate) (commercially available as Desmodur W).

In some embodiments, the equivalent ratio of the carboxylic acid, primary aminoalkyl, or secondary aminoalkyl functional groups of the Michael Adduct to isocyanate groups of the isocyanate functional material can be at least about 1:1 to about 4:1, or about 2:1.

As used herein, the term "epoxy functional material" includes compounds, monomers, oligomers and polymers comprising at least one or at least two epoxy groups. Suitable epoxy functional materials are capable of forming a covalent bond with a reactive group such as carboxy or amino functional group.

Non-limiting examples of suitable epoxy functional materials include bisphenol A-type epoxy resins, bisphenol F-type epoxy resins, novolac-type epoxy resins, alicyclic epoxy resins, glycidyl-type epoxy resins, biphenyl-type epoxy resins, naphthalene ring-containing epoxy resins, cyclopentadiene-containing epoxy resins, polyfunctional epoxy resins, and combinations thereof.

Bisphenol and biphenyl epoxy resins, which are traditionally referenced as di-epoxies, and epoxy cresol novolac resins, which are traditionally referenced as multifunctional epoxies, are useful in the present invention. For example, suitable epoxy cresol novolac resins include the following structure:

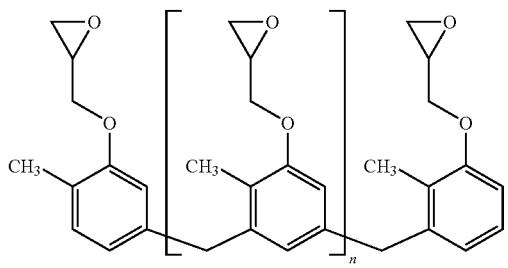

In the instance where n=0, the functionality if this structure would be 2. If n=1, the functionality, is 3, if n=4, the functionality is 4, etc.

In some embodiments, the epoxy resin is a multifunctional epoxy resin having a degree of branching within the resin backbone of at least three. These multifunctional epoxy resins are those derived from phenol and which include at least three phenolic groups branching directly from the same central carbon atom or central cluster of carbons, with a pendant oxirane group linked to each of the at least three phenolic groups. Non-limiting examples of useful multifunctional epoxy resins having a degree of branching of at least three include:

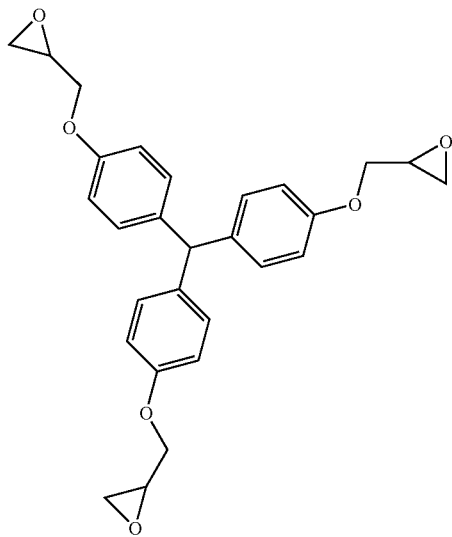

triphenylol methane triglycidyl ether (having a degree of branching of three, represented by three terminal glycidyl ether moieties branching from a central carbon atom); and

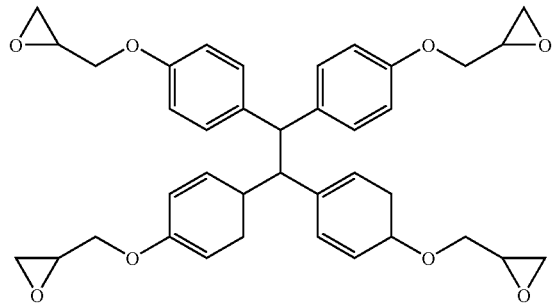

tetra glycidyl ether of tetra phenol ethane (having a degree of branching of four, represented by four terminal glycidyl ether moieties branching from a central two carbon cluster ethyl moiety).

Useful epoxy resins include those derived from tris-phenolmethane, such as triphenylol methane triglycidyl ether. Other useful resins include, but are not limited to resins of $C_6$-$C_{28}$ alkyl glycidyl ethers; polyglycidyl ethers of pyrocatechol, resorcinol, hydroquinone, 4,4'-dihydroxydiphenyl methane, 4,4'-dihydroxy-3,3'-dimethyldiphenyl methane, 4,4'-dihydroxydiphenyl dimethyl methane, 4,4'-dihydroxydiphenyl methyl methane, 4,4'-dihydroxydiphenyl cyclohexane, 4,4'-dihydroxy-3,3'-dimethyldiphenyl propane, 4,4'-dihydroxydiphenyl sulfone, and tris(4-hydroxyphenyl) methane; polyglycidyl ethers of novolacs; polyglycidyl ethers of diphenols obtained by esterifying ethers of diphenols obtained by esterifying salts of an aromatic hydrocarboxylic acid with a dihaloalkane or dihalogen dialkyl ether; polyglycidyl ethers of polyphenols obtained by condensing phenols and long-chain paraffins; polyglycidyl ethers of N,N'-diglycidyl-aniline, N,N'-dimethyl-N,N'-diglycidyl-4,4'-diaminodiphenyl methane; N,N,N',N'-tetraglycidyl-4,4'-diaminodiphenyl methane; N-diglycidyl-4-aminophenyl glycidyl ether; N,N,N',N'-tetraglycidyl-1,3-propylene bis-4-aminobenzoate; bisphenol A epoxy resin, bisphenol F epoxy resin, phenol novolac epoxy resin, cresol novolac epoxy resin, and combinations thereof. Examples of useful epoxy resins include EPON 1001F bisphenol A epoxy resin commercially available from Resolution Performance Products, EPON 2012 bisphenol A novolac epoxy resin commercially available from Resolution Performance Products, and ESCN 195XL epoxy cresol novolac resin commercially available from Sumitomo Bakelite.

In some embodiments, the equivalent ratio of the carboxylic acid, primary aminoalkyl and/or secondary aminoalkyl groups of the Michael Adduct to epoxy functional groups of the epoxy functional material can be at least about 1:1 to about 4:1, or about 2:1.

One or more curing agents or hardeners can be used to promote crosslinking of the epoxy. Non-limiting examples of suitable curing agents that can be included crosslinkable composition include amine type hardeners, phenol novolac type hardeners, cresol novolac type hardeners, dicyclopentadiene phenol type hardeners, and anhydrides. Flexible hardeners having a hydroxyl equivalent weight greater than about 150 are often desirable, such as xylock novolac type hardener. Non-limiting examples of flexible hardeners include bisphenol M commercially available from Borden Chemical, DEH 85 commercially available from Dow Chemical, Epicure P-101 amine hardener commercially available from Resolution Performance Products and 3,3',4,4'-benzophenonetetracarboxylic anhydride (BTDA). More than one type of curing agent can be included in the coating powder compositions. The curing agent is typically present in the composition of the present invention in an amount of about 1 percent by weight to about 10 percent by weight, often from about 15 percent by weight to about 6 percent by weight, based on the total weight of the crosslinkable composition.

In some non-limiting embodiments, suitable carboxylic acid functional materials include succinic acid, adipic acid, pimelic acid and azeleic acid.

In some embodiments, the equivalent ratio of the hydroxyalkyl groups of the Michael Adduct to carboxylic acid functional groups of the carboxylic acid functional material can be at least about 1:1 to about 4:1, or about 2:1.

In some non-limiting embodiments, non-limiting examples of suitable cyclic anhydride functional materials include succinic anhydride and tetrahydrophthalic anhydride.

In some embodiments, the equivalent ratio of the hydroxyalkyl, primary aminoalkyl and/or secondary aminoalkyl groups of the Michael Adduct to anhydride functional groups of the anhydride functional material can be at least about 1:1 to about 4:1, or about 2:1.

In some non-limiting embodiments, non-limiting examples of suitable acid halide functional materials include adipoyl chloride and sebacoyl chloride.

In some embodiments, the equivalent ratio of the hydroxyalkyl, primary aminoalkyl and/or secondary aminoalkyl groups of the Michael Adduct to acid halide functional groups of the acid halide functional material can be at least about 1:1 to about 4:1, or about 2:1.

In some non-limiting embodiments, the material (b) can further comprise acrylate functionality to provide groups which are capable of self-crosslinking by free radical polymerization. In some non-limiting embodiments, the free radicals can be generated by exposure of the carbonyl groups, cyano groups, phosphono groups, sulfinyl groups and/or sulfonyl groups, which are present in the Reaction Product A, to actinic radiation. The acrylate functionality can be provided by reaction of Reaction Product A with another material having acrylate functionality or acrylate functionality can be present in the material (b), for example as discussed below.

In some non-limiting embodiments, the material (b) having acrylate functionality can be selected from:

(i) at least one (meth)acrylated urethane isocyanate functional material, wherein the Michael Adduct is hydroxyalkyl, primary aminoalkyl, or secondary aminoalkyl functional;

(ii) at least one (meth)acrylated epoxy functional material, wherein the Michael Adduct is carboxylic acid, primary aminoalkyl, or secondary aminoalkyl functional;

(iii) at least one (meth)acrylated carboxylic acid functional polyester material, wherein the Michael Adduct is hydroxyalkyl functional;

(iv) at least one (meth)acrylated acid anhydride functional material, wherein the Michael Adduct is hydroxyalkyl, primary aminoalkyl, or secondary aminoalkyl functional, and (v) at least one (meth)acrylated acid halide functional material, wherein the Michael Adduct is hydroxyalkyl, primary aminoalkyl, or secondary aminoalkyl functional.

Suitable (meth)acrylated materials (b) include (meth)acrylate functional versions of any of the isocyanate functional materials, epoxy functional materials, carboxylic acid functional polyester materials, acid anhydride functional materials and acid halide functional materials discussed above.

In some non-limiting embodiments, for example, (meth)acrylated urethane isocyanate functional material can be prepared by reacting polyisocyanate with polyol to form an isocyanate functional urethane prepolymer, and then reacting the isocyanate functional urethane prepolymer with hydroxy functional acrylate. Non-limiting examples of suitable polyisocyanates are discussed above. As used herein, the term "polyol" includes compounds, monomers, oligomers and polymers comprising at least two hydroxyl groups (such as diols) or at least three hydroxyl groups (such as triols), higher functional polyols and mixtures thereof, Suitable polyols are capable of forming a covalent bond with a reactive group such as an isocyanate functional group.

Non-limiting examples of suitable polyols include hydrocarbon polyols, polyether polyols, polyester polyols and mixtures thereof. As used herein, hydrocarbon polyol means saturated aliphatic polyols, unsaturated aliphatic polyols such as olefins, alicyclic polyols and aromatic polyols.

Non-limiting examples of suitable diols include straight chain alkane diols such as ethylene glycol, diethylene glycol, triethylene glycol, tetraethylene glycol, 1,2-ethanediol, propane diols, butane diols, pentane diols, hexane diols, heptane diols, octane diols, nonane diols, decane diols, dodecane diols, octadecanediols, sorbitol, mannitol, and mixtures thereof. In some non-limiting embodiments, one or more carbon atoms in the polyol can be replaced with one or more heteroatoms, such as N, S, or O, for example sulfonated polyols, such as dithio-octane bis diol, thiodiethanol such as 2,2-thiodiethanol, or 3,6-dithia-1,2-octanediol.

Other non-limiting examples of suitable diols include those represented by the following formula:

wherein R represents $C_0$ to $C_{18}$ divalent linear or branched aliphatic, cycloaliphatic, aromatic, heterocyclic, or oligomeric saturated alkylene radical or mixtures thereof, $C_2$ to $C_{18}$ divalent organic radical containing at least one element selected from the group consisting of sulfur, oxygen and silicon in addition to carbon and hydrogen atoms; $C_5$ to $C_{18}$ divalent saturated cycloalkylene radical; or $C_5$ to $C_{18}$ divalent saturated heterocycloalkylene radical; and R' and R" can be present or absent and, if present, each independently represent $C_1$ to $C_{18}$ divalent linear or branched aliphatic, cycloaliphatic, aromatic or aryl, heterocyclic, polymeric, or oligomeric saturated alkylene radical or mixtures thereof. As used herein, "alkylene" means a difunctional group obtained by removal of a hydrogen atom from an alkyl group that is defined below. Non-limiting examples of alkylene include methylene, ethylene and propylene.

Other non-limiting examples of suitable diols include branched chain alkane diols, such as propylene glycol, dipropylene glycol, tripropylene glycol, neopentyl glycol, 2-methyl-butanediol. 2,2,4-trimethyl-1,3-pentanediol, 2-methyl-1,3-pentanediol, 2-ethyl-1,3-hexanediol, 2-methyl-1,3-propanediol, 2,2-dimethyl-1,3-propanediol, dibutyl 1,3-propanediol, polyalkylene glycols such as polyethylene glycols, and mixtures thereof.

In some non-limiting embodiments, the diol can be a cycloalkane diol, such as cyclopentanediol, 1,4-cyclohexanediol, cyclohexanedimethanols (CHDM), such as 1,4-cyclohexanedimethanol, cyclododecanediol, 4,4'-isopropylidene-biscyclohexanol, hydroxypropylcyclohexanol, cyclohexanediethanol, 1,2-bis(hydroxymethyl)-cyclohexane, 1,2-bis(hydroxyethyl)-cyclohexane, 4,4'-isopropylidene-biscyclohexanol, bis(4-hydroxycyclohexanol)methane, and 4,8-bis(hydroxymethyl)tricyclo[5.2.1.0$^{2,6}$]decane and mixtures thereof.

In some non-limiting embodiments, the diol can be an aromatic diol, such as dihydroxybenzene, 1,4-benzenedimethanol, xylene glycol, hydroxybenzyl alcohol and dihydroxytoluene; bisphenols, such as, 4,4'-isopropylidenediphenol (Bisphenol A), 4,4'-oxybisphenol, 4,4'-dihydroxybenzophenone, 4,4'-thiobisphenol, phenolphthalein, bis(4-hydroxyphenyl)methane, 4,4'-(1,2-ethenediyl)bisphenol and 4,4'-sulfonylbisphenol; hydrogenated bisphenols, halogenated bisphenols, such as 4,4'-isopropylidenebis(2,6-dibromophenol), 4,4'-isopropylidenebis(2,6-dichlorophenol) and 4,4'-isopropylidenebis(2,3,5,6-tetrachlorophenol); alkoxylated bisphenols, which can have, for example, ethoxy, propoxy, α-butoxy and β-butoxy groups; and biscyclohexanols, which can be prepared by hydrogenating the corresponding bisphenols, such as 4,4'-isopropylidene-biscyclohexanol, 4,4'-oxybiscyclohexanol, 4,4'-thiobiscyclohexanol and bis(4-hydroxycyclohexanol) methane, the alkoxylation product of 1 mole of 2,2-bis(4-hydroxyphenyl)propane (i.e., bisphenol-A) and 2 moles of propylene oxide, hydroxyalkyl terephthalates such as meta or para bis(2-hydroxyethyl)terephthalate, bis(hydroxyethyl)hydroquinone and mixtures thereof.

In some non-limiting embodiments, the diol can be an heterocyclic diol, for example a dihydroxy piperidine such as 1,4-bis(hydroxyethyl)piperazine; a diol of an amide or alkane amide [such as ethanediamide (oxamide)], for example N,N', bis(2-hydroxyethyl)oxamide; a diol of a propionate, such as 2,2-dimethyl-3-hydroxypropyl-2,2-dimethyl-3-hydroxypropionate; a diol of a hydantoin, such as bishydroxypropyl hydantoin; a diol of a phthalate, such as meta or para bis(2-hydroxyethyl)terephthalate, a diol of a hydroquinone, such as a dihydroxyethylhydroquinone; and/or a diol of an isocyanurate, such as dihydroxyethyl isocyanurate.

Non-limiting examples of trifunctional, tetrafunctional or higher polyols suitable for use include branched chain alkane polyols such as glycerol or glycerin, tetramethylolmethane, trimethylolethane (for example 1,1,1-trimethylolethane), trimethylolpropane (TMP) (for example 1,1,1-trimethylolpropane), erythritol, pentaerythritol, dipentaerythritol, tripentaerythritol, sorbitan, alkoxylated derivatives thereof (discussed below) and mixtures thereof.

In some non-limiting embodiments, the polyol can be a cycloalkane polyol, such as trimethylene bis(1,3,5-cyclohexanetriol); or an aromatic polyol, such as trimethylene bis(1,3,5-benzenetriol).

Further non-limiting examples of suitable polyols include the aforementioned polyols which can be alkoxylated derivatives, such as ethoxylated, propoxylated and butoxylated. In alternate non-limiting embodiments, the following polyols can be alkoxylated with from 1 to 10 alkoxy groups: glycerol, trimethylolethane, trimethylolpropane, benzenetriol, cyclohexanetriol, erythritol, pentaerythritol, sorbitol, mannitol, sorbitan, dipentaerythritol and tripentaerythritol. Non-limiting examples of suitable alkoxylated polyols include ethoxylated trimethylolpropane, propoxylated trimethylolpropane, ethoxylated trimethylolethane, and mixtures thereof.

In some non-limiting embodiments, the polyol can be an unsaturated aliphatic polyol such as NISSO GI-1000 hydroxy terminated, hydrogenated 1,2-polybutadiene (HPBD resin) having a calculated number average molecular weight of about 1500 and a hydroxyl value of about 60-120 KOH mg/g commercially available from Nippon Soda Co Ltd.

In some non-limiting embodiments, the polyol for use in the present invention can be an SH-containing material, such as a dithiol or polythiol. Non-limiting examples of suitable polythiols can include, but are not limited to, aliphatic polythiols, cycloaliphatic polythiols, aromatic polythiols, heterocyclic polythiols, polymeric polythiols, oligomeric polythiols and mixtures thereof. As used herein, the terms "thiol," "thiol group," "mercapto" or "mercapto group" refer to an —SH group which is capable of forming a thiourethane linkage, (i.e., —NH—C(O)—S—) with an isocyanate group or a dithiourethane linkage (i.e., —NH—(C(S)—S—) with an isothiocyanate group.

In some embodiments, the polyol can be one or more polyether polyol(s). Non-limiting examples of polyether polyols include poly(oxyalkylene) polyols or polyalkoxylated polyols. Poly(oxyalkylene) polyols can be prepared in accordance with known methods. In a non-limiting embodiment, a poly(oxyalkylene) polyol can be prepared by condensing an alkylene oxide, or a mixture of alkylene oxides, using an acid- or base-catalyzed addition with a polyhydric initiator or a mixture of polyhydric initiators, such as ethylene glycol, propylene glycol, glycerol, and sorbitol. Compatible mixtures of polyether polyols can also be used. As used herein, "compatible" means that two or more materials are mutually soluble in each other so as to essentially form a single phase. Non-limiting examples of alkylene oxides can include ethylene oxide, propylene oxide, butylene oxide, amylene oxide, aralkylene oxides, such as styrene oxide, mixtures of ethylene oxide and propylene oxide. In some non-limiting embodiments, polyoxyalkylene polyols can be prepared with mixtures of alkylene oxide using random or step-wise oxyalkylation. Non-limiting examples of such poly (oxyalkylene)polyols include polyoxyethylene polyols, such as polyethylene glycol, and polyoxypropylene polyols, such as polypropylene glycol.

Other polyether polyols include block polymers such as those having blocks of ethylene oxide-propylene oxide and/or ethylene oxide-butylene oxide. In some non-limiting embodiments, the polyether polyol comprises a block copolymer of the following formula:

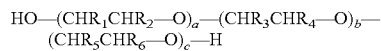

where $R_1$ through $R_6$ can each independently represent hydrogen or methyl; and a, b, and c can each be independently selected from an integer from 0 to 300, wherein a, b, and c are selected such that the number average molecular weight of the polyol is less than about 32,000 grams/mole, or less than about 10,000 grams/mole, as determined by GPC.

In some non-limiting embodiments, polyalkoxylated polyols can be represented by the following general formula:

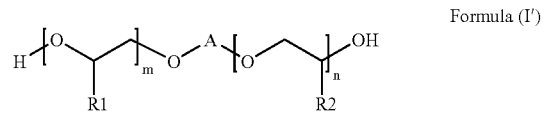

Formula (I')

wherein m and n can each be a positive integer, the sum of m and n being from 5 to 70; $R_1$ and $R_2$ are each hydrogen, methyl or ethyl; and A is a divalent linking group such as a straight or branched chain alkylene which can contain from 1 to 8 carbon atoms, phenylene, and $C_1$ to $C_9$ alkyl-substituted phenylene. The values of m and n can, in combination with the selected divalent linking group, determine the molecular weight of the polyol. Polyalkoxylated polyols can be prepared by methods that are known in the art. In a non-limiting embodiment, a polyol such as 4,4'-isopropylidenediphenol can be reacted with an oxirane-containing material such as ethylene oxide, propylene oxide or butylene oxide, to form what is commonly referred to as an ethoxylated, propoxylated or butoxylated polyol having hydroxyl functionality.

In some non-limiting embodiments, the polyether polyol can be PLURONIC ethylene oxide/propylene oxide block copolymers, such as PLURONIC R and PLURONIC L62D, and/or TETRONIC tetra-functional block copolymers based on ethylene oxide and propylene oxide, such as TETRONIC R, which are commercially available from BASF Corp.

As used herein, the phrase "polyether polyols" also can include poly(oxytetramethylene)diols prepared by the polymerization of tetrahydrofuran in the presence of Lewis acid catalysts such as, but not limited to boron trifluoride, tin (IV) chloride and sulfonyl chloride.

In some embodiments, non-limiting examples of suitable polyether polyols include poly(propylene oxide)diols, copoly (ethylene oxide-propylene oxide)diols, and poly(tetramethylene oxide)diols.

In some embodiments, the polyether polyol can be POLY-MEG® 2000 polytetramethylene ether glycol (linear diol having a backbone of repeating tetramethylene units connected by ether linkages and capped with primary hydroxyls having a molecular weight of about 1900-2100 and a hydroxyl number of about 53.0 to about 59.0), commercially available from Lyondell.

In other embodiments, the polyether polyol can be TER-ATHANE® 1000 polytetramethylene ether glycol is a blend of linear diols in which the hydroxyl groups are separated by repeating tetramethylene ether groups: $HO(CH_2CH_2CH_2CH_2—O—)_nH$ in which n averages 14 and having a hydroxyl number of 107-118, commercially available from INVISTA, or POLYMEG® 1000.

In some non-limiting embodiments, the polyol can be one or more polyester polyol(s). In some embodiments, the polyester polyol is selected from the group consisting of polyester glycols, polycaprolactone polyols, polycarbonate polyols and mixtures thereof Non-limiting examples of suitable polyester polyols include any well-known di-, tri-, or tetrahydroxy-terminated polyesters such as polylactone polyesters and polyester polyols produced by the polycondensation reactions of dicarboxylic acids or their anhydrides with di-, tri-, or tetra-alcohols.

Non-limiting examples of such polyester polyols include polyester glycols, polycaprolactone polyols, polycarbonate polyols and mixtures thereof. Polyester glycols can include the esterification products of one or more dicarboxylic acids having from four to ten carbon atoms, such as, but not limited to adipic, succinic or sebacic acids, with one or more low molecular weight glycols having from two to ten carbon atoms, such as, but not limited to ethylene glycol, propylene glycol, diethylene glycol, 1,4-butanediol, neopentyl glycol, 1,6-hexanediol and 1,10-decanediol. Esterification procedures for producing polyester polyols are described, for example, in the article D. M. Young et al., "Polyesters from Lactone," Union Carbide F-40, p. 147.

Non-limiting examples of polycaprolactone polyols include those prepared by condensing caprolactone in the presence of difunctional active hydrogen material such as water or low molecular weight glycols, for example ethylene glycol and propylene glycol. Non-limiting examples of suitable polycaprolactone polyols can include CAPA polycaprolactone polyols commercially available from Solvay Chemical of Houston, Tex., such as CAPA 2085 linear polyester diol derived from caprolactone monomer, terminated by primary hydroxyl groups, and having a mean molecular weight of 830 and a typical OH value of 135 mg KOH/g, and the TONE series from Dow Chemical of Midland, Mich., such as TONE 0201, 0210, 0230 and 0241. In some non-limiting embodiments, the polycaprolactone polyol has a molecular weight ranging from about 500 to about 2000 grams per mole, or about 500 to about 1000 grams per mole.

Non-limiting examples of polycarbonate polyols include aliphatic polycarbonate diols, for example those based upon alkylene glycols, ether glycols, alicyclic glycols or mixtures thereof. In some embodiments, the alkylene groups for preparing the polycarbonate polyol can comprise from 5 to 10 carbon atoms and can be straight chain, cycloalkylene or combinations thereof. Non-limiting examples of such alkylene groups include hexylene, octylene, decylene, cyclohexylene and cyclohexyldimethylene. Suitable polycarbonate polyols can be prepared, in non-limiting examples, by reacting a hydroxy terminated alkylene glycol with a dialkyl carbonate, such as methyl, ethyl, n-propyl or n-butyl carbonate, or diaryl carbonate, such as diphenyl or dinaphthyl carbonate, or by reacting of a hydroxy-terminated alkylene diol with phosgene or bischoloroformate, in a manner well-known to those skilled in the art. Non-limiting examples of suitable polycarbonate polyols include POLY-CD 210 hydroxyl-terminated 1000 MW poly(1,6-hexanediol)carbonate polyol commercially available from Arch Chemical.

Mixtures of any of the above polyols can be used.

In some non-limiting embodiments, the polyol can have a number average molecular weight of about 100 to about 10,000 grams/mole, or about 500 to about 5,000 grams/mole, or about 600 to about 3,500 grams/mole.

In some embodiments, the polyol can comprise about 10 to about 90 weight percent of the reactants used for preparing the urethane, or about 30 to about 70 weight percent of the reactants, or about 35 to about 65 weight percent of the reactants.

As discussed above, the isocyanate functional urethane prepolymer can be reacted with at least one hydroxy functional acrylate. Non-limiting examples of suitable hydroxy functional (meth)acrylates include hydroxyethyl aerylate, hydroxypropyl acrylate, hydroxybutyl acrylate, hydroxyethyl methacrylate, hydroxypropyl methacrylate, hydroxybutyl methacrylate and mixtures thereof. Other non-limiting examples of suitable hydroxy functional (meth)acrylates include 2-hydroxyethyl acrylate, 2-hydroxypropyl acrylate, 2-hydroxyethyl methacrylate, pentaerythritol triacrylate (PETA), and 4-hydroxybutyl acrylate.

In some non-limiting embodiments, the composition comprises the Reaction Product A, which is capable of forming free radicals upon exposure to actinic radiation. Self-crosslinking can be initiated by exposure of the Reaction Product A to actinic radiation to generate the free radicals which react with the crosslinkable groups.

To facilitate polymerization, in some embodiments, the composition can further comprise one or more free radical initiators, if desired. Non-limiting examples of suitable free radical initiators include benzophenone, 1-hydroxycyclohexyl phenyl ketone, 2,2-dimethoxy-2-phenyl acetophenone (such as IRGACURE 651 available from Ciba) and combinations thereof (such as the former two in a 1:1 by weight ratio available from Ciba under the tradename IRGACURE 500). Other useful flee radical initiators available from Ciba include 2-benzyl-2-N,N-dimethylamino-1-(4-morpholino phenyl)-1-butane (IRGACURE 369), 2-methyl-1-[4(methylthio)phenyl]-2-morpholino propane-1-one (IRGACURE 907), 2-hydroxyl-2-methyl-1-phenyl-propane-1-one (DAROCURE, 1173), 1-hydroxycyclohexyl phenyl ketone, 2,2-dimethoxy-2-phenyl acetophenone, bis(2,6-dimethoxybenzoyl-2,4,4-trimethyl pentyl)phosphine oxide, bis(2,4,6-trimethyl benzoyl)phenyl phosphine oxide, 4-(2-hydroxyethyoxy)phenyl-(2-hydroxy-2-methylpropyl)ketone, 2,4,6-trimethylbenzoyl-diphenylphosphine oxide, and combinations thereof.

The free radical initiator(s) can be present in an amount of up to about 5 percent by weight, such as about 0.01 to about 3 percent by weight, for example 0.5 to 2 percent by weight of the composition.

The composition can further comprise one or more cationic photoinitiators, such as those having as a counter ion a phosphorous or antimony metal complex with the appropriate number of halogen (such as fluorine) atoms per metal atom. In the context of surface mount electronic component attachment, see U.S. Pat. No. 4,916,805 (Elrich), which discloses certain photoinitiators having counter ions, such as $PF_6^-$, $BF_4^-$, $AsF_6^-$ and $SbF_6^-$.

Other cationic photoinitiators suitable for use herein include onium salts represented by the general formula:

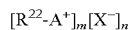

wherein:

$R^{22}$ is one or more aromatic radicals which can be the same or different, for example aryl, alkaryl, and aralkyl groups, including fused ring structures comprising an aromatic ring, which may be optionally substituted with a linear, branched or cyclic $C_8$ to $C_{20}$ radical of alkyl, alkylene, alkoxy, alkyleneoxy, a nitrogen, oxygen or sulfur heterocyclic radical of 4 to 6 carbon atoms in the ring; or a mixture thereof, $A^+$ is selected from iodonium cation mono-substituted with $C_1$ to $C_{20}$ alkyl or aryl optionally substituted with $C_1$ to $C_{20}$ alkyl or alkoxy and sulfonium cation di-substituted with $C_1$ to $C_{20}$ alkyl or aryl optionally substituted with $C_1$ to $C_{20}$ alkyl or alkoxy or a mixture thereof;

$X^-$ is a non-basic, non-nucleophilic anion, examples of which include $PF_6^-$, $BF_4^-$, $AsF_6^-$, $SbF_6^-$, $ClO_4^-$, $CF_3SO_3^-$, $(C_5F_5)_4B^-$ and the like;

m ranges from 1 to 3; and n ranges from 1 to 3, wherein m is equal to n.

Non-limiting examples of such cationic photoinitiators include diaryliodonium, triarylsulfonium, diaryliodosonium, triarylsulfoxonium, dialkylphenacylsulfonium and alkylhydroxyphenylsulfonium salts. See e.g. U.S. Pat. No. 4,219,654 (Crivello); U.S. Pat. No. 4,058,400 (Crivello); U.S. Pat. No. 4,058,401 (Crivello) and U.S. Pat. No. 5,079,378 (Crivello). Other examples include triarylsufonium and diaryliodonium salts containing non-nucleophilic counterions such as diphenyl iodonium chloride, diphenyl iodonium hexafluorophosphate, 4,4-dioctyloxydiphenyl iodonium hexafluorophosphate, triphenylsulfonium tetrafluoroborate, diphenyltolylsulfonium hexafluorophosphate, phenylditolylsulfonium hexafluoroarsenate, and diphenyl-thiophenoxyphenylsulfonium hexafluoroantimonate, and those available from Sartomer, Exton, Pa. under the SARCAT tradename, such as SARCAT CD 1010 [triaryl sulfonium hexafluoroantimonate (50% in propylene carbonate)]: SARCAT DC 1011 [triaryl sulfonium hexafluorophosphate (50% n-propylene carbonate)]; SARCAT DC 1012 (diaryl iodonium hexafluoroantimonate); SARCAT K185 [triaryl sulfonium hexafluorophosphate (50% in propylene carbonate)] and SARCAT SR1010 [triarylsulfonium hexafluoroantimonate (50% in propylene carbonate)]; and SARCAT SR1012 (diaryliodonium hexafluoroantimonate), and those available from Dow under the CYRACURE tradename, such as UVI-6976 mixture of triarylsulfonium hexafluoroantimonate salts in propylene carbonate, the triarylsulfonium hexafluoroantimonate salts being selected from:

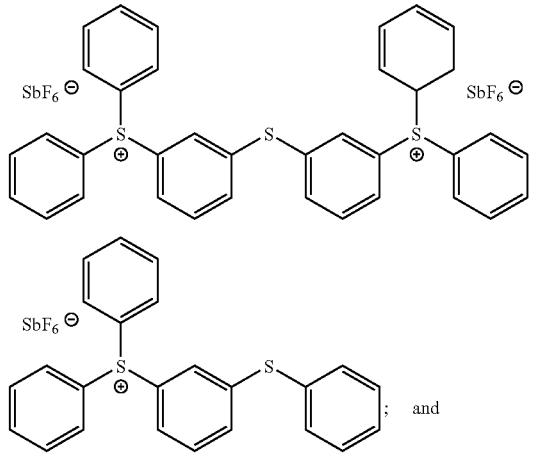

UVI-6992 (mixed triarylsulfonium hexafluorophosphate salts).

Other useful cationic photoinitiators include UV 9385C (an alkylphenyl iodonium hexafluorophosphate salts) and UV 9390C (an alkylphenyl iodonium/hexafluoroantimonate salt) available from General Electric Corporation; CGI 552 (an alkylphenyl iodonium hexafluorophosphate salt); and RADCURE UVACure 1590 available from UCB, Belgium; and a cationic photoinitiator for silicone-based release coatings, whose counter ion contains fluoride atoms covalently bound to aromatic carbon atoms of the counter ion, such as $B(C_6F_5)_4$ available from Rhodia Chemie. See International Patent Application Nos. PCT/TR97/00566 and PCT/FR98/00741. See also Rhone-Poulenc Chemie's U.S. Pat. No. 5,550,265 (Castellanos), U.S. Pat. No. 5,668,192 (Castellanos), U.S. Pat. No. 6,147,184 (Castellanos), and U.S. Pat. No. 6,153,661 (Castellanos).

Other useful cationic photoinitiators include those having a core cation of structure I below:

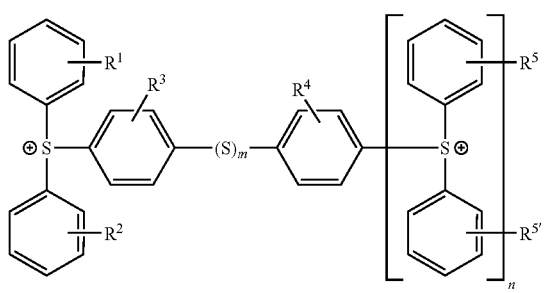

where $R^1$, $R^2$, $R^3$, $R^4$, $R^5$ and $R^{5'}$ are each independently selected from H, $C_{1-6}$ alkyl, $C_{2-6}$ alkenyl, halogen, hydroxyl and carboxyl, n is 0-3 and m is 0-1, such as for example those represented by structures II and III:

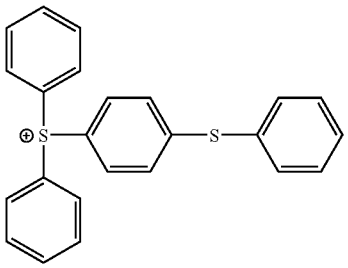

II

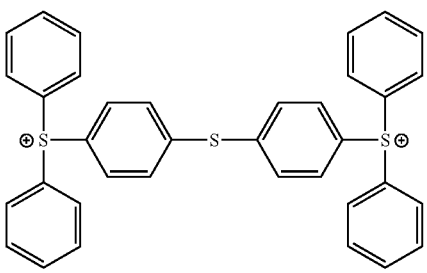

III

Other useful cationic photoinitiators include those having core cations of structures IV, V, and VI:

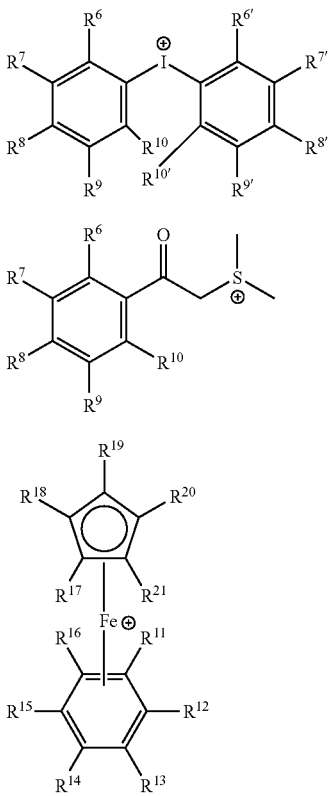

IV

V

VI where:

for structure IV, $R^6$, $R^7$, $R^8$, $R^9$ and $R^{10}$ are each independently selected from H, alkyl, such as from 1 to 5 carbon atoms, halogen, hydroxyl, and carboxyl;

for structure V, $R^6$, $R^7$, $R^8$, $R^9$, $R^{10}$, $R^{6'}$, $R^{7''}$, $R^{8'}$, $R^{9'}$, and $R^{10'}$ are each independently selected from H, alkyl, such as from 1 to 5 carbon atoms, halogen, hydroxyl, and carboxyl; and for structure VI, $R^{11}$, $R^{12}$, $R^{13}$, $R^{14}$, $R^{15}$, $R^{16}$, $R^{17}$, $R^{18}$, $R^{19}$, $R^{20}$, and $R^{21}$ are each independently selected from H, alkyl, such as from 1 to 5 carbon atoms, halogen, hydroxyl, and carboxyl.

Other useful cationic photoinitiators having core cations within structure IV, V and VI include those represented by structures VII(a) and VII(b), VIII and IX (the latter of which is available under the tradename IRGACURE 261 from Ciba Specialty Chemicals), respectively:

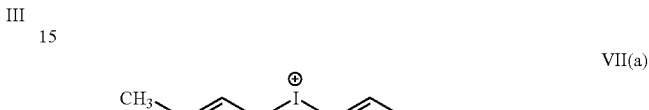

VII(a)

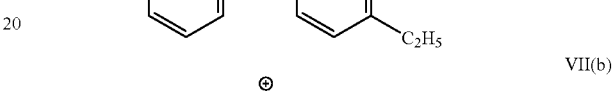

VII(b)

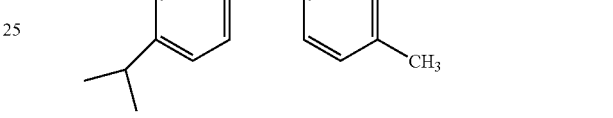

VIII

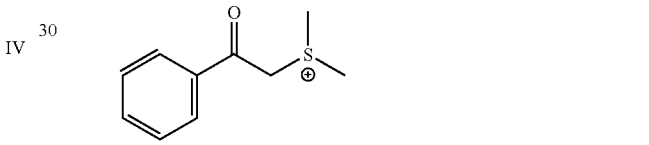

IX

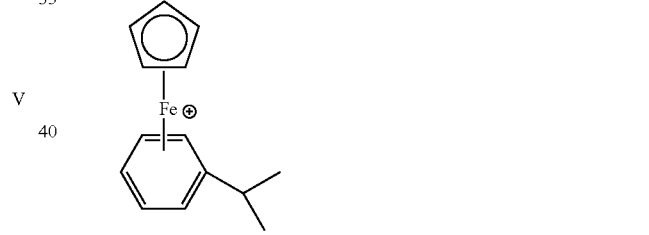

Structure VII(b) is the cationic portion of the RHODOSIL 2074 photoinitiator, available from Rhodia Chemie, whose chemical name is tolylcumyl iodonium tetrakis(pentafluorophenyl)borate (CAS No. 178233-72-2).

The cationic photoinitiator can be present in an amount of up to about 5 percent by weight, such as about 0.01 to about 3, for example 0.5 to 2 percent by weight on a basis of total weight of the composition.

In some embodiments, the composition can further comprise one or more visible light photoinitiators and/or photosensitizers. An example of such a material is camphorquinone ("CPQ"), though others such as 9-fluorene carboxylic acid peroxyesters, visible light [blue] photoinitiators, IRGACLURE 784DC (photoinitiator based on substituted titanocenes), and combinations thereof, may be used.

Other suitable photoinitiator systems triggered in the visible range of electromagnetic spectrum may be used and include those disclosed in: U.S. Pat. No. 4,505,793 (Tamoto) which discloses a combination of a 3-keto-substituted cumarin compound and active halogeno compound photopolymerization initiators that cure by exposure to light having wavelengths ranging between about 180 nm and 600 nm;

European Patent Publication No. EP 0 369 645 A1 which discloses a three-part photoinitiator system which includes a trihalomethyl substituted-s-triazine, a sensitizing compound capable of absorbing radiation in the range of about 300-1000 nm (such as ketones; coumarin dyes; xanthene dyes; 3H-xanthen-3-one dyes; acridine dyes; thiazole dyes; thiazine dyes; oxazine dyes; azine dyes; methane and polymethine dyes; porphyrins; aromatic polycyclic hydrocarbons; merocyanines; and squarylium dyes) and an electron donor (such as ethers; ferrocene: sulfinic acids and their salts; salts of ferrocyanide; ascorbic acid and its salts; dithiocarbamic acid and its salts; salts of xanthates; salts of ethylene diamine tetraacetic acid: and salts of tetraphenylboronic acid); European Patent Publication No. EP 0 563 925 A1 which discloses photopolymerization initiators including a sensitizing compound that is capable of absorbing radiation in the range of about 250-1000 nm (such as cyanine dye, merocyanine dye, coumarin dye, ketocoumarin dye, (thio)xanthene dye, acridine dye, thiazole dye, thiazine dye, oxazine dye, azine dye, squarylium dye, porphyrin dye, triaryl methane dye, (poly) methane dye, and aromatic polycyclic hydrocarbons); U.S. Pat. No. 5,395,862 (Neckers) which discloses fluorone initiator systems including a coinitiator that is capable of accepting an electron from the excited fluorone species (such as onium salts, nitrohalomethanes and diazosulfones); U.S. Pat. No. 5,451,343 (checkers) which discloses fluorone and pyronin-Y derivatives as initiators that absorb light at wavelengths of greater than 350 nm: and U.S. Pat. No. 5,545,676 (Palazzotto) which discloses a three-part photoinitiator system including an arylidonium salt, a sensitizing compound and an electron donor which cures under UV or visible light, each of the foregoing references being incorporated by reference herein.

These photoinitiators triggered in the visible range of the electromagnetic spectrum may be present in amounts of about 0.1% to about 10% by weight, for example 0.5% to about 5% by weight on a basis of total weight of the composition.

When used, these photoinitiators can permit the inventive compositions to cure dry-to-the-touch, forming reaction products with tack-free exterior surfaces.

The inclusion of such a photoinitiator broadens the energy sources available to cure the inventive composition. For example, a LED device generating radiation in or about 470 mm may be used to cure the inventive compositions, such as is described in International Patent Publication No. WO 04/011848 and International, Patent Application No. PCT/US2005/016900, each of which is incorporated by reference herein.

The composition can further comprise one or more inorganic filler components, such as reinforcing silicas or fused silicas that may be untreated or treated so as to alter the chemical nature of their surface. Virtually any reinforcing fused silica may be used. Alternatively, the inorganic filler component may be fumed silica, which may impart thixotropy to the composition. Other useful materials for the inorganic filler component include those comprising aluminum oxide, silicon nitride, aluminum nitride, silica-coated aluminum nitride and micronized quartz, provided they are not basic in nature.

Various adhesion promoters may be used in the curable compositions of the invention, particularly where the composition is intended as an adhesive or coating. Adhesion promoters may include acid functional monomers such as acrylic acid or methacrylic acid, and silane adhesion promoters such as glycidoxypropyltrimethoxysilane, methacryloxypropyltrimethoxysilane, methacryloxypropyltriacetoxysilane, and acryloxypropyltrimethoxysilane, and various unsaturated nitrogen-containing compounds such as N,N'-dimethylacrylamide, acryloyl morpholine, N-methyl-N-vinyl acetamide, N-vinyl caprolactam, N-vinylphthalimide, Uracil, and N-vinylpyrrolidone. Adhesion promoters may be used alone or in combination. The adhesion promoter(s) may be used in the adhesive composition of the invention in an amount from about 0.5% to about 30% by weight of the composition, or about 1% to about 20% by weight, or about 2% to about 10% by weight.

The compositions of the present invention can be applied to a substrate by conventional means, including spray, curtain, dip pad, roll-coating and brushing procedures. The compositions can be applied to any acceptable substrate such as wood, metal, glass, fabric, paper, fiber, plastic, and the like.

The applied radiation curable composition can be cured by any of the known actinic radiation curing methods such as exposure to ultraviolet light, X-rays, alpha particles, electron beam, or gamma rays. As used herein, "actinic radiation" means radiation that produces photochemical effects, such as ultraviolet light or electron beam radiation. As used herein, "photoinitiation" means the photoproduction of a free radical or ion capable of initiating a chain reaction such as a polymerization. Irradiation can be performed using any of the known and commonly available types of radiation curing equipment, for example, curing may be done by low, medium, or high pressure mercury arc lamps. Curing can be carried out in air or in an inert atmosphere such as nitrogen or argon. Exposure time required to cure the composition varies somewhat depending on the specific formulation, type and wavelength of radiation, energy flux, and film thickness. Those skilled in the art of radiation technology will be able to determine the proper curing time for any particular composition. Generally, the cure time is rather short, that is, less than about 60 seconds.

The inventive compositions are useful as adhesives and coatings and are capable of demonstrating significant improvement in physical properties, such as adhesive strength or tensile strength, when used to bond metals and plastic substrates, without adversely affecting cure rate.

The present invention also provides methods for bonding a pair or more of substrates, using the compositions so described. In some embodiments, the methods of bonding substrates, comprise the steps of: (a) providing a first substrate; (b) providing a second substrate; (c) providing a composition as described above on at least one of the first or second substrates; (d) exposing the composition to conditions sufficient to initiate cure thereof, and (e) mating the first and second substrates, and allowing the composition to achieve greater than 85% of its ultimate strength.

In other embodiments, the present invention provides methods for attaching a first substrate to a second substrate, comprising the steps of: (a) applying a composition as described above to the first substrate; (b) activating the composition prior to or after application thereof through exposure to radiation in the electromagnetic spectrum; and (c) positioning the other substrate onto the one substrate; and (d) optionally, curing the composition at a temperature between 60° C. and 160° C.

One such method includes the steps of applying such a composition to at least one substrate, activating the composition prior to, during or after application thereof through exposure to radiation in the electromagnetic spectrum, such as UV radiation at wavelength in a range of 254-405 nm, to such an extent that a desired initial tackiness is maintained and no skin formation on the surface of the composition occurs; positioning the one substrate onto the other substrate;

and allowing the composition to cure to bond the pair or more substrates, and optionally, speeding cure of the composition by exposure to a temperature between about 60 and about 175° C., such as about 80 to about 150° C.

In some embodiments, the inventive compositions are capable of achieving an open time of from 1 second to about five minutes (before gelling occurs rendering it unsuitable for adhesive applications), and developing greater than about 85% of its ultimate cure after a period of time of 24 hours at room temperature.

The following examples are presented to further illustrate the invention, without intending to narrow or depart from its scope.

EXAMPLES

Example A

Example A describes the synthesis of novel hydroxyl-functional compounds derived from active methylene compounds (Examples 1-3), the use of these materials for the preparation of self-initiating UV curable acrylated urethane resins by a new synthetic route (Example 6-8) and the UV cured properties of the resins as determined by UV spectral analyses and photorheometry (Examples 9-12). It also describes the syntheses of novel vinyl ether and tert-butyl ester functionalized β-diketones and their use as UV photoinitiators (Examples 4, 5, 13 and 14). Also, we have found that acrylated oligomers derived from cyanoacetates undergo efficient self-initiated curing on UV exposure (Examples 15 & 16). These materials were prepared according to the established (prior art) procedures and highlight the limitations of that method.

Example 1

Synthesis of bis-(2'-hydroxyethyl)-4,4-diacetyl azelate

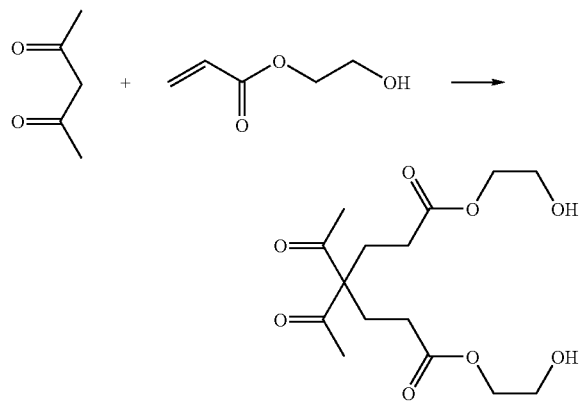

2,4-Pentanedione (25.0 g; 247.2 mmol) and triethylamine (2.4 g; 24.7 mmol) were added to a 250 ml, glass reaction flask equipped with magnetic stirrer, thermocouple and pressure compensating addition funnel. The mixture was stirred and cooled to near 0° C. 2-Hydroxyethyl acrylate (57.5 g; 494.4 mmol) was added slowly while maintaining the temperature near 0° C. After the addition was complete, the mixture was warmed to about 40° C. and stirred for 72 hours, at which stage IR analysis confirmed complete consumption of acrylate double bonds by the absence of absorption at 1630 cm$^{-1}$. The mixture was cooled to room temperature, dissolved in ethanol (about 50 mL) and treated with acidic alumina (20 g) to remove the amine catalyst. The mixture was stirred and filtered to provide a clear solution. The solvent was removed by distillation under reduced pressure (40° C.; ~200 torr) followed by heating in an oven under vacuum (80° C.; ~0.4 torr) to constant weight. The product was isolated as a golden-colored oil that solidified upon standing at ambient temperature (72.3 g; 88%; m.p. 69° C.). The hydroxyl number was found to be 364 mg KOH/g, close to the theoretical value of 338 mg KOH/g calculated for the required product, bis-(2-hydroxyethyl)-4,4-diacetyl azelate. The structure was confirmed by spectral analyses.

IR (neat, ATR crystal). Absorbance maxima (cm$^{-1}$): 3449 (w; O—H); 2967 (w; C—H); 1725 (s; C=O ester); 1683 (s; C0 ketone). $^1$H NMR (300 MHz: CDCl$_3$). δ (ppm): 4.22 (m, 4H, —C(O)O—CH$_2$—); 3.80 (m, 4H, —CH$_2$—OH); 2.40-1.50 (m, 14H, C—CH$_2$—CH$_2$—C(O)— and —CH$_3$). $^{13}$C NMR (75 MHz; CDCl$_3$) δ (ppm): 206.5 (C=O AcAc); 173.0 (C=O ester); 69.0 (—CH$_2$O); 66.5 (α-C AcAc); 61.0 (—CH$_2$OH); 29.0 (CH$_2$—CH$_2$—C); 27.0 (C(=O)—CH$_2$)—; 26.0 (—CH$_3$).

Example 2

Synthesis of bis-(2'-hydroxyethyl)-4-cyano-4-methyl carboxylate)azelate

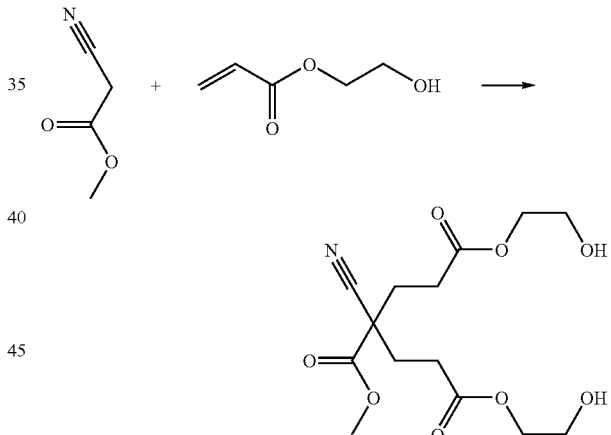

Methyl cyanoacetate (12.0 g; 120 mmol), triethylamine (1.84 g; 18.0 mmol) and 2-hydroxyethyl acrylate (27.9 g; 240 mmol) were reacted together according to the procedure described in Example 1. After heating at 40° C. for 44 hours and treatment with alumina, a pale yellow oil (37.1 g; 93%) was isolated. The hydroxyl number was found to be 315 mg KOH/g, close to theoretical value of 339 mg KOH/g calculated for the required product, bis-(2'-hydroxyethyl)-4-cyano-4-(methyl carboxylate)azelate. The structure was confirmed by spectral analyses.

IR (neat, ATR crystal). Absorbance maxima (cm$^{-1}$): 3445 (w, O—H); 2957 (w, C—H); 2250 (w, CN); 1729 (C=O) $^1$H NMR (300 MHz; CDCl$_3$). δ (ppm): 4.45-4.15 (m, 4H; —C(O)O—); 4.00-3.65 (m, 7H; —CH$_2$—OH and —OCH$_3$), 2.80-1.90 (m, 8H; C—CH$_2$—CH$_2$—C(=O)—). $^{13}$C NMR (75 MHz; CDCl$_3$). δ (ppm): 171.5 (C=O butyl ester); 168.0 (C=O methyl ester), 118.0 (—CN); 66.5 (—CH$_2$O); 60.5

(CH$_2$OH); 54.0 (OCH$_3$); 48.0 (α-C cyanoacetate); 32.0 (CH$_2$—CH$_2$—C); 30.0 (C(=O)—CH$_2$).

Example 3

Synthesis of bis-(4'-hydroxybutyl)-4,4-diacetyl azelate

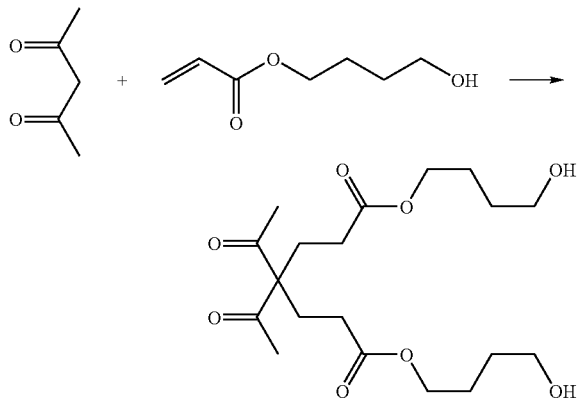

2,4-pentanedione (10.1 g; 100 mmol) and 4-hydroxybutyl acrylate (36.0 g; 200 mmol) were added to a 250 mL glass reaction flask fitted with magnetic stirrer, thermocouple, and cooling bath. The mixture was stirred and 1,1,3,3-tetramethylguanidine (1.97 g; 17 mmol) was added slowly at such a rate that the temperature did not exceed 40° C. After the addition was complete, the mixture was heated to 40° C. and stirred for 4 hours. Additional 2-hydroxybutyl acrylate (7.2 g; 40 mmol) was added and the mixture stirred for a further 24 hours. The mixture was purified by the procedure described in Example 1 and provided crude bis-(4'-hydroxybutyl)-4,4-diacetyl azelate as a pale yellow liquid (37.9 g; 98%) having an hydroxyl number of 210 mg KOH/g (theoretical value=289 mg KOH/g). The structure of the crude product was confirmed by spectral analyses.

IR (neat, ATR crystal). Absorbance maxima (cm$^{-1}$): =3397 (w; O—H); 2943 (w; C—H); 1727 (s; C=O ester); 1690 (shoulder, C=O ketone). $^1$H NMR (300 MHz; CDCl$_3$). δ (ppm): 4.10 (m, —C(O)O—CH$_2$—); 3.65 (m, —CH$_2$—OH); 3.05-1.50 (m) $^{13}$C NMR (75 MHz: CDCl$_3$). δ (ppm): 211.0 (C=O AcAc); 173.0 (C=O ester); 64.0 (—CH$_2$O and (αC AcAc); 62.0 (CH$_2$OH); 50.5 (s); 31.0 (CH$_2$—CH$_2$—C); 29.0 (C(=O)—CH$_2$); 26.0 (—CH$_3$).

Example 4

Synthesis of bis-(tert-butyl)-4,4-diacetyl azelate

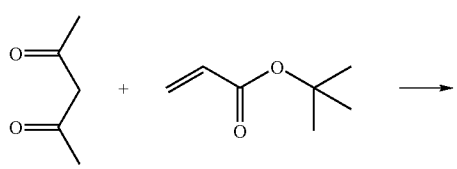

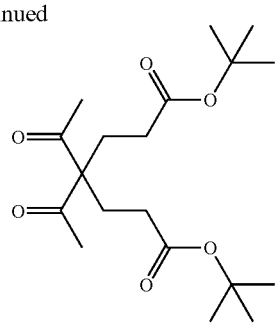

2,4-pentanedione (10.11 g; 100 mmol), tert-butyl acrylate (30.76 g; 240 mmol) and 1,4-dioxane (100 ml) were added to a 250 ml, glass reactor equipped with magnetic stirrer, thermocouple and cooling ice bath. The mixture was stirred and 1,1,3,3-tetramethylguanidine (1.97 g; 17 mmol) was added slowly at such a rate that the temperature did not exceed 40° C. After the addition was complete, the mixture was heated to 40° C. and stirred for 12 hours. On cooling, a white precipitate was formed and collected by filtration. The precipitate was dissolved in ethanol (25 mL) and the solution treated with acidic alumina and purified according to the procedure described in Example 1. The product, bis-(tert-butyl)-4,4-diacetyl azelate, was isolated as a white crystalline material (32.3 g; 91%) with m.p. of 91° C. The structure of the product was confirmed by spectral analyses.

IR (neat, ATR crystal). Absorbance maxima (cm$^{-1}$): 2977 (w, C—H)); 1728 (m, C=O ester); 1690 (m, C=O ketone). $^1$H NMR (300 MHz, CDCl$_3$). δ (ppm): 2.25-1.95 (m, 14H; C—CH$_2$—CH$_2$—C(=O)— and —CH$_3$ AcAc); 1.60-1.30 (m, 18H; C—(CH$_3$)$_3$). $^{13}$C NMR (75 MHz; CDCl$_3$). δ (ppm): 206.5 (C=O AcAc); 172.0 (C=O ester); 81.0 (C—(CH$_3$)$_3$—)); 68.5 (α-C AcAc); 29.5 (CH$_2$—CH$_2$—C); 28.0 (C—(CH$_3$)$_3$—)); 27.0 (C(=O)—CH$_2$); 26.0 (—CH$_3$).

Example 5

Synthesis of bis-[2'-(2"-vinyloxyethoxy)ethyl]-4,4-diacetyl azelate

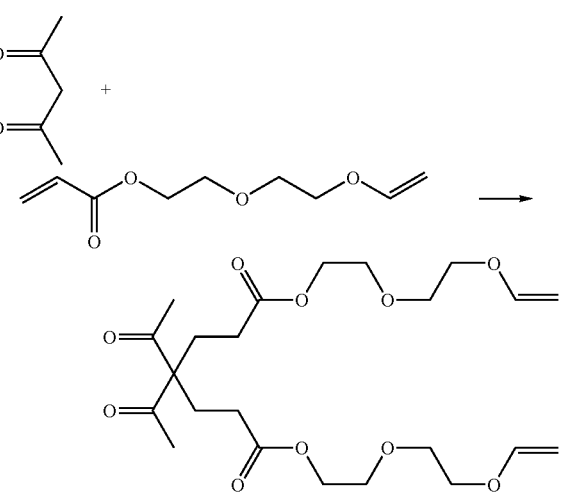

The above compound was prepared by reaction of 2,4-pentanedione (10.11; 100 mmol), 2-(2'-Vinyloxy ethoxy)

ethyl acrylate (45.5 g; 245 mmol) and 1,1,3,3-tetramethylguanidine (1.97 g; 17 mmol) according to the procedure of Example 3. The product was isolated as an orange-colored oil (after filtration through activated carbon) (41.3 g; 88%). The structure of the product was confirmed by spectral analyses.

IR (neat, ATR crystal). Absorbance maxima (cm$^{-1}$: 2935 (w, C—H)); 1731 (s, C=O ester); 1698 (m, C=O ketone); 1630 (shoulder) and 1619 (m, —CH=CH$_2$). $^1$H NMR (300 MHz, CDCl$_3$). δ (ppm): 6.55-6.45 (m, 2H, —OCH=CH$_2$); 4.30-3.60 (m, 20H, OCH=CH$_2$) and —CH$_2$—O—); 2.20-2.00 (m, 14H, —CH$_2$— and C(=O)CH$_3$). $^{13}$C NMR (75 MHz; CDCl$_3$). δ (ppm): 205.5 (C=O AcAc); 172.5 (C=O ester); 151.5 (—O—CH=); 86.5 (—CH=CH$_2$); 70.0-68.0 (m, O—CH$_2$—); 67.0 (α-C AcAc); 63.5 (CH$_2$OH); 28.0 (CH$_2$—CH$_2$—C); 27.0 (C(=O)—CH$_2$); 26.0 (—CH$_3$).

Example 6

Synthesis of Polyurethane Resin ("UR-1")

Polycaprolactone diol (CAPA 2085 supplied by Solvay; 70.08 g; 0.173 equivalents), isophorone diisocyanate (38.43 g, 0.346 equivalents), isobornyl aerylate (29.64 g) and dibutyltin dilaurate (0.06 g) were added to a 500 mL glass reactor equipped with heating bath, thermocouple, dry air sweep and addition funnel. The contents were stirred and heated at 75° C. for 1.5 hours under dry air atmosphere. 2-Hydroxyethyl acrylate (10.05 g; 0.086 moles) was added and mixture stirred and heated at 75° C. for an additional hour. The residual isocyanate concentration was determined by the reaction of an aliquot of the reaction mixture with excess dibutylamine followed by potentiometric titration with standard hydrochloric acid solution and an equivalent amount of bis-(2'-hydroxyethyl)-4,4-diacetyl azelate (Example 1; 12.68 g; 0.076 equivalents) was added followed by bismuth octoate (0.07 g). The mixture was stirred for an additional 2.0 hours at 75° C. at which stage an additional amount of bismuth octoate (0.07 g) was added. Heating and stirring were continued for an additional 6 hours at which stage residual isocyanate, as determined by IR analysis, was less than 0.2 weight %. The resin, isolated as a clear, slightly yellow syrup that solidified to a gum at room temperature, comprised a blend of 82% by weight polyurethane oligomers with a theoretical average molecular weight of 3,100 and 18% by weight isobornyl acrylate (IBOA).

Example 7

Synthesis of Polyurethane Resin ("UR-2")

Polycaprolactone diol (CAPA 2085 supplied by Solvay: 70.08 g; 0.173 equivalents), isophorone diisocyanate (38.42 g, 0.346 equivalents), isobornyl acrylate (29.63 g) and dibutyltin dilaurate (0.06 g) were added to a 500 mL glass reactor equipped with heating bath, thermocouple, dry air sweep and addition funnel. The contents were stirred and heated at 75° C. for 1.5 hours under dry air atmosphere. 2-Hydroxyethyl acrylate (10.04 g; 0.086 moles) was added and the mixture was stirred and heated at 75° C. for an additional hour. The residual isocyanate concentration was determined as described in Example 6 and an equivalent amount of bis-(4'-hydroxybutyl)-4,4-diacetyl azelate (Example 3; 20.79 g; 0.078 equivalents) was added followed by bismuth octoate (0.21 g). The mixture was stirred for an additional 3.0 hours at 75° C., at which stage all isocyanate was consumed (as determined by IR analysis). The product, isolated as a viscous yellow-colored resin, comprised a blend of 82% by weight polyurethane oligomers with a theoretical average molecular weight of 3,300 and 18% by weight isobornyl acrylate (IBOA).

Example 8

Synthesis of Polyurethane Resin ("UR-3")

Polycaprolactone diol (CAPA 2085 supplied by Solvay; 90.32 g; 0.223 equivalents), isophorone diisocyanate (49.53 g, 0.446 equivalents), isobornyl acrylate (38.20 g) and dibutyltin dilaurate (0.08 g) were added to a 500 mL glass reactor equipped with heating bath, thermocouple, dry air sweep and addition funnel. The contents were stirred and heated at 75° C. for 1.5 hours under dry air atmosphere. 2-Hydroxyethyl acrylate (12.95 g; 0.111 moles) was added and mixture stirred and heated at 75° C. for an additional hour. The residual isocyanate concentration was determined as described in Example 6 and an equivalent amount of bis-(2'-hydroxyethyl)-4-cyano-4-(methyl carboxylate)azelate (Example 2; 17.49 g; 0.098 equivalents) was added followed by bismuth octoate (0.09 g). The mixture was stirred for an additional 2.0 hours at 75° C., at which stage an additional amount of bismuth octoate (0.17 g) was added. Heating and stirring were continued for an additional 8 hours at which stage residual isocyanate, as determined by IR analysis, was less than 0.2 weight %. The product, isolated as a viscous resin, comprises a blend of 82% by weight polyurethane oligomers with a theoretical average molecular weight of 3,100 and 18% by weight isobornyl aerylate (IBOA).

Example 9

UV-Visible Spectral Analyses of Polyurethane Resins

UV-visible light spectral analysis of polyurethane resins UR-1, UR-2 and UR-3 showed that all resins had absorbance in the region 220-340 nm with shoulder peaks around 286 nm. Irradiation with light from this region of the wavelength spectrum was therefore necessary to ensure that photoinitiated curing can take place.

Example 10

UV Curing of Polyurethane Resin UR-1

The UV cure activity of the resin UR-1 was monitored using an Anton Paar Physica MCR 301 UV photorheometry. The experiments were performed using parallel plate geometry and an oscillatory applied stress. Unless otherwise specified, the experiments were carried out at room temperature (25° C.) using a 25 mm diameter oscillating aluminum plate and a transparent fixed glass or quartz plate at 1 mm gap, 1% strain and a frequency of 1 Hz. Loss modulus (G"), storage modulus (G'), and damping factor (tan δ) were monitored for each composition as a function of time as a particular cure profile (defined by lamp intensity and duration of irradiation) was applied to each sample.

The glass plates used in the rheometer transmit only UV radiation with a wavelength greater than 320 nm; quartz plates transmit all radiation above 200 nm. The intensity of the transmitted radiation was adjusted via a shutter setting on the rheometer's tight source. Deformation (% strain) and frequency are fixed on the rheometer at settings corresponding to the uncured sample's linear viscoelastic region (LVR). If the sample is photocurable, G' and G" will both increase dramatically upon irradiation, eventually crossing at a point defined as the gel point of the sample (tan δ=1).

A sample of the resin UR-1 was evaluated using a glass bottom plate (no UV transmission below 320 nm). Irradiation conditions included either continuous irradiation at 23 mW/cm$^2$ or 30 seconds of irradiation at 200 mW/cm$^2$ followed by dark monitoring. For comparative purposes, a structurally similar urethane acrylate (with no incorporated Michael adduct) was blended with 18% by weight IBOA and the resulting composition also evaluated by photorheometry using continuous irradiation at 23 mW/cm$^2$ (Control). The lamp is turned on at t=16.5 seconds. The results are shown in FIG. 1 as a plot of storage modulus (G') and tan δ (G"/G') as a function of UV exposure time. Resin UR-1 had a gel time of about 2 minutes; whereas the Control composition showed no gelation or any significant change in viscosity even after 1 hour of continuous irradiation. Resin UR-1 demonstrated effective photocure while the control showed no response to irradiation.

Example 11

UV Curing of Polyurethane Resin UR-2

Figure 2:
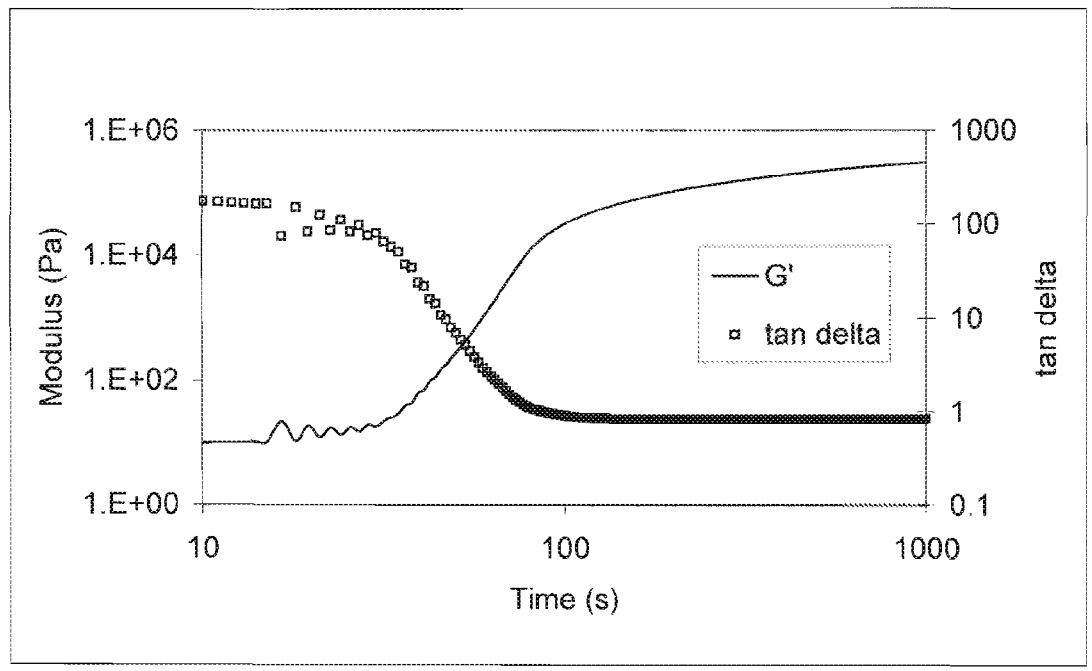
FIG. 2 is a graph of storage modulus (G') and tan δ (G"/G') as a function of UV exposure time for resin UR-2 according to the present invention.

Resin UR-2 was analyzed by photorheometry as described in Example 10 using a light intensity of 100 mW/cm$^2$, a 60 second exposure time and a quartz plate. The irradiation was carried out under a nitrogen purge. Rheometry data are shown in FIG. 2. The time required to reach the gel point was 73 seconds, the plateau storage modulus (G') was 0.575 MPa.

Example 12

UV Curing of Polyurethane Resin UR-3

Figure 3:
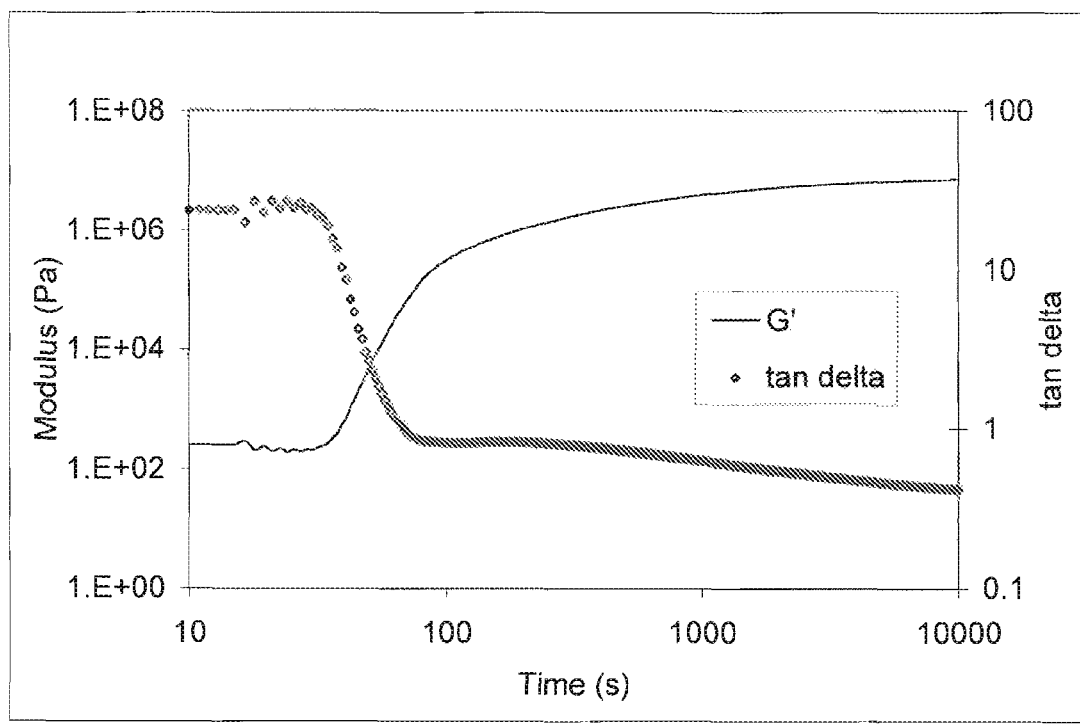
FIG. 3 is a graph of storage modulus (G') and tan δ (G"/G') as a function of UV exposure time for resin UR-3 according to the present invention.

Resin UR-3 was analyzed by photorheometry using the same conditions as described in Example 11 for UR-2. It reached the gel point in 56 seconds; its plateau modulus was 7.55 MPa. The rheometry data are shown in FIG. 3.

Example 13

Substituted Diketone Photoinitiators

A photocurable composition was prepared by blending together the components described in Table 1.

TABLE 1

Photocurable composition with diketone photoinitiator

| Component | Weight % |
|---|---|
| Trimethylolpropane trimethacrylate (TMPTMA) | 93.0 |
| bis-(tert-butyl)-4,4-diacetyl azelate (Example 4) | 7.0 |

Figure 4:
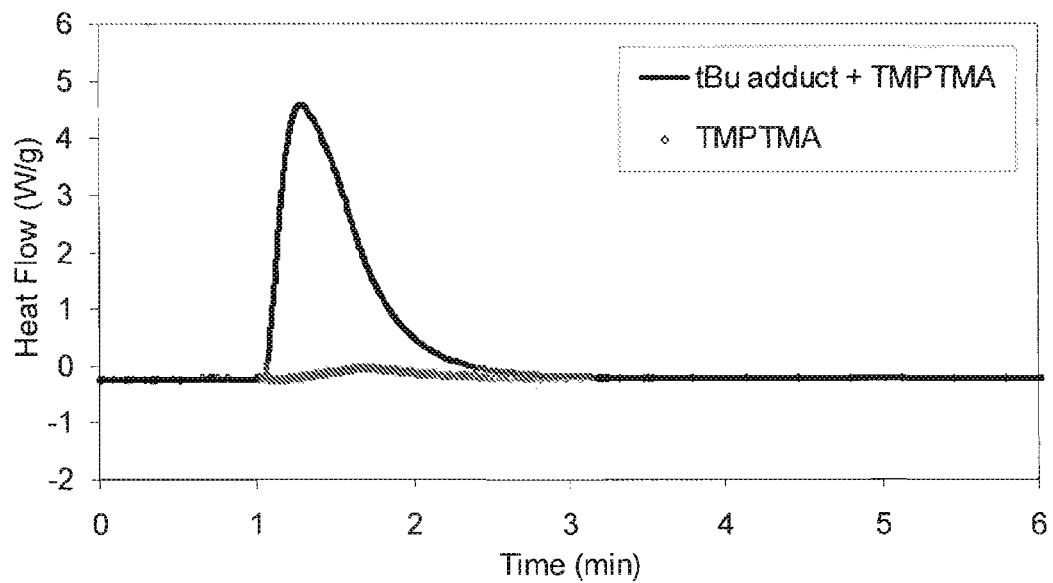
FIG. 4 is a photo DSC (differential scanning calorimeter) showing photocure of the composition of Example 13 according to the present invention.

The UV light initiated curing of the formulation was examined using a photo DSC (differential scanning calorimeter), equipped with a medium pressure mercury arc lamp and quartz cover plate. On exposure to UV light for 30 seconds at an incident intensity of 60 mW/cm2 (365 nm), the formulation underwent a rapid curing reaction with an exotherm peak after 17 seconds of irradiation. An enthalpy of 169 J/g was recorded. In contrast, when the methacrylate monomer alone was irradiated under the same conditions, it gave an exotherm peak after 42 seconds and an enthalpy of 8 J/g, corresponding to 5% of normalized cure. The results, presented in FIG. 4, demonstrate that the α,α-disubstituted β-diketone is an effective photoinitiator of acrylate curing.

Example 14

Photoinitiated Copolymerization of (Meth)Acrylate and Vinyl Ether Monomers

Photocurable compositions were prepared by blending together the components described in Table 2.

TABLE 2

Photocurable (meth)acrylate/vinylether compositions at 4.4/1 and 3.9/1 for TMPTA (Blend A) and TMPTMA (Blend B) equivalent weight ratios, respectively

| | Weight % | |
|---|---|---|
| Component | A | B |
| Trimethylolpropane triacrylate (TMPTA) | 65 | — |
| Trimethylolpropane trimethacrylate (TMPTMA) | — | 65 |
| bis-[2'-(2"-vinyloxyethoxy)ethyl]-4,4-diacetyl azelate (Example 5) | 35 | 35 |

The UV light initiated curing of the Formulations A and B were examined using photo DSC as described in Example 13 and an exposure time of 60 seconds. The acrylate product (Formulation A) had a peak exotherm of 34 seconds and an enthalpy of 296 J/g. In contrast, when the acrylate monomer alone was irradiated under the same conditions, it had an exotherm peak after 67 seconds and enthalpy of 15 J/g, corresponding to a conversion of 5% normalized to Blend A.

The methacrylate product gave a peak exotherm of 40 seconds and an enthalpy of 110 J/g. In contrast, when the methacrylate monomer alone was irradiated under the same conditions, it gave an exotherm peak after 34 seconds, but the enthalpy of 10 J/g. The results are summarized in Table 3 and show the degrees of cure for each of the compositions normalized to that of Blend A for formulations containing TMPTA and to the composition of Example 13 for formulations containing TMPTMA.

TABLE 3

PhotoDSC results for vinylether/(meth)acrylate hybrid systems

| Formulation | Time to peak max (s) | Enthalpy (J/g) | Normalized conversion (%) |
|---|---|---|---|
| Blend A | 34 | 296 | 100 |
| TMPTA | 67 | 15 | 5 |
| Blend B | 40 | 110 | 65 |
| TMPTMA | 34 | 10 | 6 |

The significantly higher enthalpy and conversions observed for acrylate/vinyl ether blend A compared to methacrylate/vinyl ether blend B can be attributed to the copolymerization of the vinyl ether and acrylate components in A which does not occur to any significant extent in B. The normalized conversion in B, 65%, scales closely with the amount of methacrylate in the formulation.

Figure 5:
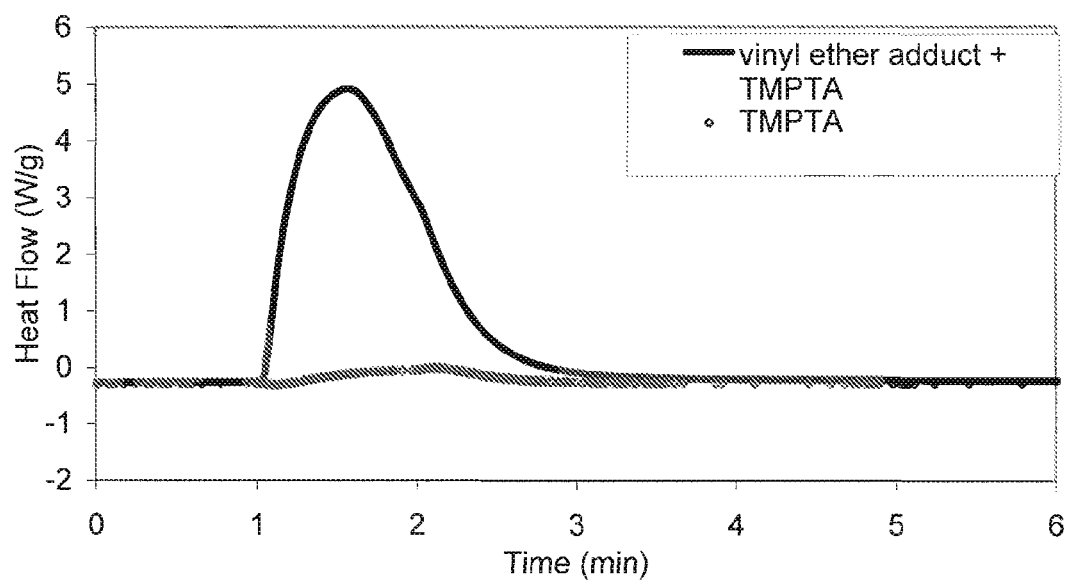
FIG. 5 is a photo DSC (differential scanning calorimeter) showing photocure of a composition of Blend A of Example 14 according to the present invention.

This result demonstrates that the vinyl ether functionalized with (α,α-disubstituted β-diketone can be used as a self-initiating photopolymer system for acrylate resins by means of a copolymerization reaction. Although it also functions as a photoinitiator for methacrylates, there does not appear to be any significant copolymerization in that system. FIG. 5 shows the photo DSC traces for Blend A and corresponding control sample, TMPTA (shutter opened after 60 seconds).

Example 15

Synthesis and Self-Initiated Photopolymerization of Cyanoacetate-Extended Trimethylolpropane Triacrylate

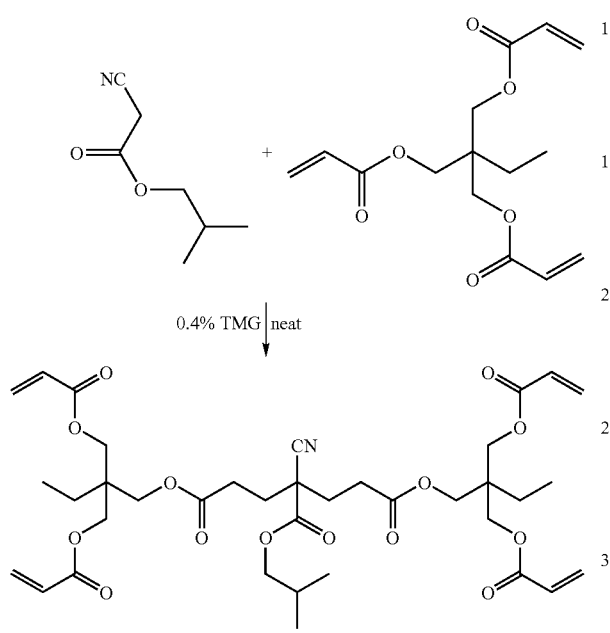

Trimethylolpropane triacrylate (49.51 g, 0.167 moles, 0.50 equivalents) and 1,1,3,3-tetramethylguanidine (0.38 g) were added to a 150 mL glass reactor fitted with a mechanical stirrer, thermocouple, heating mantel and pressure compensating addition funnel. Isobutyl cyanoacetate (10.07 g, 0.071 moles, 0.14 equivalents) was added dropwise to the rapidly stirred reaction mixture at such a rate as to maintain the temperature in the range 40-50° C. An intense blue color developed during the addition of the cyanoacetate, which rapidly dissipated. As the reaction proceeded, there was a very significant increase in viscosity and some gel was observed to form on the sidewall of the reactor where rapid mixing was not possible. The viscous non-gel led component was separated for testing.

Films of the neat resin, about 1.0 mm in film thickness, were prepared on microscope glass slides and exposed to UV light from (a) the full spectrum of a high intensity mercury lamp (Zeta 7216) and (b) partial spectrum from a low intensity mercury lamp filtered through a dichroic mirror (Oriel projector). The incident light intensities, measured with a UV-power puck radiometer (supplied by EIT Products Inc.) at the location of the film surfaces, are detailed in Table 4.

TABLE 4

Light intensities of Zeta and Oriel lamps at surface of films

| Wavelength range | Intensity (mW/cm$^2$) | |
|---|---|---|
| (nm) | Zeta 7216 | Oriel projector |
| 200-280 (UVC) | 28 | 0 |
| 280-320 (UVB) | 190 | 0 |
| 320-400 (UVA) | 200 | 6 |
| 400-450 (UVV) | 120 | 5 |

The Zeta lamp emits high intensity light throughout the UV and in the blue region of the wavelength spectrum, whereas the Oriel lamp has relatively low emissions predominately in the UVA and blue regions. The curing of the resin films were monitored under these conditions and compared with similar films of unmodified trimethylolpropane triacrylate (TMPTA) alone. The results are presented in Table 5.

TABLE 5

UV curing times for resin films

| | Exposure time for cure (seconds) | | | |
|---|---|---|---|---|
| | Zeta 7216 | | Oriel projector | |
| | Bulk | Surface | Bulk | Surface |
| Resin | 15 | 10 | 300 | >300 |
| TMPTA | >60 | >60 | >300 | >300 |

Bulk cure was determined as the minimum exposure time required to cure throughout the entire depth of the film with no observable liquid on the supporting glass slide after removal of the cured film. Surface cure was determined as the minimum exposure required to obtain a hard, non-tacky surface on the film. The result clearly shows that the cyanoacetate modified resin has excellent cure properties under high intensity full-spectrum UV irradiation compared to unmodified acrylate monomer. The product is also sensitive to a small degree under low intensity UVA and UVV irradiation, but surface cure was not achieved in this case.

Example 16

Synthesis and Self-Initiated Photopolymerization of Cyano Acetate Extended Hexanediol Diacrylate

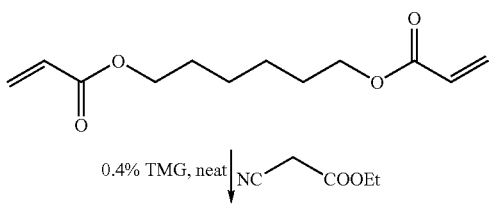

-continued

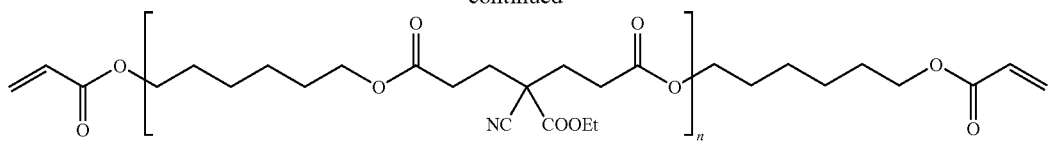

Hexanediol diacrylate (45.21 g, 0.20 moles, 0.4 equivalents) and 1,1,3,3-tetramethylguanidine (0.29 g) were added to a 150 mL glass reactor fitted with a mechanical stirrer, thermocouple, heating mantel and pressure compensating addition funnel. Ethyl cyanoacetate (11.33 g, 0.1 moles, 0.2 equivalents) was added dropwise to the rapidly stirred reaction mixture at such a rate as to maintain the temperature in the range of 40-50° C. After the addition was complete, the mixture was stirred for 0.5 hours and cooled.

The UV curing of the resin was examined by exposure to UV light from Zeta 7216 lamp as described in Example 15. Bulk cure was obtained after 90 seconds exposure and surface cure (tack-free) after 180 seconds. The results indicate that the extended cyanoacetate resin is self-initiating on exposure to UV light, although with a reduced activity compared to the resin product of Example 15.

What is claimed is:

1. A reaction product prepared from reactants consisting of:
   (a) at least one Michael addition donor material comprising two or more active methylene hydrogens; and
   (b) at least one monoacrylate capable of reacting with a Michael addition donor, the monoacrylate comprising at least one functional group selected from the group consisting of hydroxy, hydroxyalkyl, amino, aminoalkyl, carboxy, carboxyalkyl, cyano, and cyanoalkyl groups, wherein the reaction product is capable of forming free radicals upon exposure to actinic radiation.

2. The reaction product according to claim 1, wherein the equivalent ratio of the monoacrylate (b) to the Michael addition donor material (a) is at least 2:1.

3. The reaction product according to claim 1, wherein the Michael addition donor material (a) comprises two electron-withdrawing groups, each electron withdrawing group being independently selected from the group consisting of carbonyl groups, cyano groups, phosphono groups, sulfinyl groups and sulfonyl groups.

4. The reaction product according to claim 3, wherein the Michael addition donor material (a) comprises at least one cyano group and is selected from the group consisting of malononitrile, ethyl cyanoacetate, methyl cyanoacetate and isobutyl cyanoacetate.

5. The reaction product according to claim 3, wherein the carbonyl group is selected from the group consisting of acyl groups, keto groups, amide groups, ester groups and thiocarbonyl groups.

6. The reaction product according to claim 5, wherein the Michael addition donor material (a) comprises at least one ester group and is selected from the group consisting of dimethyl acetonedicarboxylate, diethyl acetonedicarboxylate, 2,2-dimethyl-1,3-dioxane-4,6-dione and malonic diesters.

7. The reaction product according to claim 5, wherein the Michael addition donor material (a) comprises at least one acyl group and is selected from the group consisting of alkyl ketones, heteroalkyl ketones, cycloalkyl ketones, heterocyclyl ketones, aryl ketones and heteroaryl ketones.

8. The reaction product according to claim 7, wherein the alkyl ketone is selected from the group consisting of 2,4-pentanedione, and 2,4,6-heptanetrione.

9. The reaction product according to claim 7, wherein the heteroalkyl ketone is selected from the group consisting of acetoacetamide, methyl acetoacetate, ethyl acetoacetate, butyl acetoacetate, butanediol diacetoacetate, ethylhexyl acetoacetate, lauryl acetoacetate, hexanediol diacetoacetate, neopentyl glycol diacetoacetate, trimethylolpropane triacetoacetate, glycerin triacetoacetate, pentaerythritol tetraacetoacetate, ethyleneglycol monoacetoacetate mono(meth)acrylate and 1-(triethylphosphonomethyl)methyl ketone.

10. The reaction product according to claim 7, wherein the cycloalkyl ketone is selected from the group consisting of 4,4-dimethylcyclohexane-1,3-dione and 5,5-dimethylcyclohexane-1,3-dione.

11. The reaction product according to claim 7, wherein the aryl ketone is selected from the group consisting of dibenzoylmethane, benzoylacetone, benzoylacetamide and benzoylacetanilide.

12. The reaction product according to claim 1, wherein the monoacrylate is a hydroxy functional mono acrylate selected from the group consisting of hydroxymethyl(meth)acrylate, hydroxyethyl(meth)acrylate, hydroxypropyl(meth)acrylate, hydroxybutyl(meth)acrylate, hydroxypentyl(meth)acrylate and hydroxypropoxypropyl(meth)acrylate.

13. The reaction product according to claim 1, wherein the monoacrylate is a protected amino functional monoacrylate selected from the group consisting of 2-methylcarbamatoalkyl acrylate, ethylcarbarmatoalkyl acrylate, propylcarbamatoalkyl acrylate, butylcarbamatoalkyl acrylate, and isocyanato ethyl (meth)acrylate.

14. The reaction product according to claim 1, wherein the monoacrylate is a carboxy functional monoacrylate selected from the group consisting of acrylic acid, betacarboxyethyl acrylate, and the reaction product of a hydroxy functional monoacrylate with a cyclic anhydride.

15. The reaction product according to claim 1, wherein the reaction product is prepared from 2,4-pentanedione and 2-hydroxyethyl acrylate.

16. The reaction product according to claim 1, wherein the reaction product is prepared from 2,4-pentanedione and 2-hydroxypropyl acrylate.

17. The reaction product according to claim 1, wherein the reaction product is prepared from 4,4-dimethyl-1,3-cyclohexanedione and 2-hydroxybutyl acrylate.

18. A composition comprising:
   (a) the reaction product of claim 1; and
   (b) at least one material selected from the group consisting of:
      (i) at least one isocyanate functional material, wherein the reaction product according to claim 1 is hydroxyalkyl, primary aminoalkyl, or secondary aminoalkyl functional;
      (ii) at least one epoxy functional material, wherein the reaction product according to claim 1 is carboxylic acid, primary aminoalkyl, or secondary aminoalkyl functional;

(iii) at least one carboxylic acid functional material, wherein the reaction product according to claim 1 is hydroxyalkyl functional;

(iv) at least one anhydride functional material, wherein the reaction product according to claim 1 is hydroxyalkyl, primary aminoalkyl, or secondary aminoalkyl functional; and (v) at least one acid halide functional material, wherein the reaction product according to claim 1 is hydroxyalkyl, primary aminoalkyl, or secondary aminoalkyl functional.

19. A composition according to claim 18, wherein the at least one material (b) is selected from the group consisting of:

(i) at least one (meth)acrylated urethane isocyanate functional material, wherein the reaction product according to claim 1 is hydroxyalkyl, primary aminoalkyl, or secondary aminoalkyl functional;

(ii) at least one (meth)acrylated epoxy functional material, wherein the reaction product according to claim 1 is carboxylic acid, primary aminoalkyl, or secondary aminoalkyl functional;

(iii) at least one (meth)acrylated carboxylic acid functional polyester material, wherein the reaction product according to claim 1 is hydroxyalkyl functional;

(iv) at least one (meth)acrylated acid anhydride functional material, wherein the reaction product according to claim 1 is hydroxyalkyl, primary amino alkyl, or secondary aminoalkyl functional; and (v) at least one (meth)acrylated acid halide functional material, wherein the reaction product according to claim 1 is hydroxyalkyl, primary amino alkyl, or secondary aminoalkyl functional.

20. A composition according to claim 18, comprising the reaction product (A) of:

(a) the reaction product of claim 1; and (b) the at least one material (b), wherein the reaction product (A) is capable of forming free radicals upon exposure to actinic radiation.

21. The composition according to claim 20, wherein the reaction product (A) further comprises residual crosslinkable groups capable of reacting with the free radicals.

22. The composition according to claim 21, wherein self-crosslinking of reaction product (A) can be initiated by exposure of the composition to actinic radiation to generate the free radicals which react with residual crosslinkable groups.

23. A crosslinked polymer composition obtained by exposing the composition of claim 21 to actinic radiation.

24. A method for at least partially crosslinking the composition of claim 21 comprising the step of exposing the composition of claim 21 to actinic radiation.

25. The method according to claim 24, wherein the actinic radiation is UV light.

26. A reaction product prepared from reactants comprising:

(a) at least one Michael addition donor material comprising two or more active methylene hydrogens; and (b) at least one Michael addition acceptor material (b) which is a hydroxy functional acrylamide is selected from the group consisting of N-methylol acrylamide and N-(2-hydroxyethyl)acrylamide.

27. A reaction product prepared from reactants comprising:

(a) at least one Michael addition donor material comprising at least one Michael Addition donor phosphono functional group; and (b) at least one material capable of reacting with the at least one Michael addition donor phosphono functional group, the material comprising at least one Michael addition acceptor, wherein the reaction product is capable of forming free radicals upon exposure to actinic radiation.

28. The reaction product according to claim 27, wherein the material (b) is a monoacrylate, diacrylate or polyacrylate.

29. The reaction product according to claim 28, wherein the material (b) is selected from the group consisting of trimethylolpropane triacrylate, trimethylolpropane trimethacrylate and hexanediol diacrylate.

30. A composition comprising:

(a) the reaction product of claim 27; and (b) at least one material selected from the group consisting of:

(i) at least one isocyanate functional material, wherein the reaction product according to claim 27 is hydroxyalkyl, primary aminoalkyl, or secondary aminoallyl functional;

(ii) at least one epoxy functional material, wherein the reaction product according to claim 27 is carboxylic acid, primary aminoallyl, or secondary aminoalkyl functional;

(iii) at least one carboxylic acid functional material, wherein the reaction product according to claim 27 is hydroxyalkyl functional;

(iv) at least one anhydride functional material, wherein the reaction product according to claim 27 is hydroxyalkyl, primary aminoalkyl, or secondary aminoalkyl functional;

(v) at least one acid halide functional material, wherein the reaction product according to claim 27 is hydroxyalkyl, primary aminoalkyl, or secondary aminoalkyl functional; and (vi) at least one haloalkyl functional material, wherein the reaction product according to claim 27 is hydroxyalkyl, primary aminoalkyl, or secondary aminoalkyl functional.

31. A composition according to claim 30, comprising the reaction product (A) of:

(a) the reaction product of claim 27; and (b) the at least one material (b), wherein the reaction product (A) is capable of forming free radicals upon exposure to actinic radiation.

32. The composition according to claim 31, wherein the reaction product (A) further comprises residual crosslinkable groups capable of reacting with the free radicals.

33. A crosslinked polymer composition obtained by exposing the composition of claim 32 to actinic radiation.

34. A reaction product prepared from reactants comprising:

(a) at least one cyano functional Michael addition donor material comprising two or more active methylene hydrogens; and (b) at least one monoacrylate capable of reacting with a Michael addition donor, the monoacrylate comprising at least one functional group selected from the group consisting of hydroxy, hydroxyalkyl, amino, aminoalkyl, carboxy, carboxyalkyl, cyano, and cyanoalkyl groups, wherein the reaction product is capable of forming free radicals upon exposure to actinic radiation.

35. A reaction product prepared from reactants comprising:

(a) at least one Michael addition donor material comprising two or more active methylene hydrogens; and (b) at least one mono-functional Michael Acceptor capable of reacting with a Michael addition donor, the mono-functional Michael Acceptor having one Michael Acceptor group selected from the group consisting of maleimide, cinnamate, crotonate, acrylamide, vinyl phosphate and vinyl sulfonate, the mono-functional Michael Acceptor having at least one additional functional group selected from the group consisting of hydroxy, hydroxyalkyl, amino, aminoalkyl, carboxy, carboxyalkyl, cyano, and cyanoalkyl groups, wherein the reaction product is capable of forming free radicals upon exposure to actinic radiation.

* * * * *